(12) United States Patent
Armitage

(10) Patent No.: US 11,291,564 B2
(45) Date of Patent: Apr. 5, 2022

(54) MODULAR DEVICE AND INTERFACE DESIGN

(71) Applicant: Cambridge Bio-Augmentation Systems Limited, Cambridgeshire (GB)

(72) Inventor: Oliver Armitage, Cambridgeshire (GB)

(73) Assignee: BIOS HEALTH LTD, Cambridgeshire (GB)

(*) Notice: Subject to any disclaimer, the term of this patent is extended or adjusted under 35 U.S.C. 154(b) by 102 days.

(21) Appl. No.: 15/764,307

(22) PCT Filed: Sep. 28, 2016

(86) PCT No.: PCT/GB2016/053010
§ 371 (c)(1),
(2) Date: Mar. 28, 2018

(87) PCT Pub. No.: WO2017/055836
PCT Pub. Date: Apr. 6, 2017

(65) Prior Publication Data
US 2019/0053920 A1      Feb. 21, 2019

(30) Foreign Application Priority Data

Sep. 28, 2015  (GB) ..................................... 1517134
Sep. 28, 2015  (GB) ..................................... 1517135

(51) Int. Cl.
*A61F 2/80* (2006.01)
*A61F 2/54* (2006.01)
(Continued)

(52) U.S. Cl.
CPC .................. *A61F 2/80* (2013.01); *A61F 2/54* (2013.01); *A61F 2/70* (2013.01); *A61F 2/72* (2013.01);
(Continued)

(58) Field of Classification Search
CPC ...... A61F 2/80; A61F 2/54; A61F 2/70; A61F 2/72; A61F 2002/7887; A61F 2002/802; A61L 27/12; A61L 2300/412
(Continued)

(56) References Cited

U.S. PATENT DOCUMENTS 4,158,895 A    6/1979  Reswick et al.
8,591,599 B1 * 11/2013  Kaliki .................. A61B 5/6828
                                              600/372
(Continued)

FOREIGN PATENT DOCUMENTS

CN    103519924 A    1/2014
CN    103945800 A    7/2014
(Continued)

OTHER PUBLICATIONS

Combined Search and Examination Report dated Feb. 29, 2016, regarding GB Application No. GB1517135.8.
(Continued)

*Primary Examiner* — Jerrah Edwards
*Assistant Examiner* — Aren Patel
(74) *Attorney, Agent, or Firm* — Arent Fox LLP

(57) ABSTRACT

Herein described is an osseointegrated interface device for engagement with an amputated limb including the skin comprising: a cap portion engageable with an osseointegrated device; wherein the cap portion comprises a surrounding flange; and wherein in use the surrounding flange receives the skin of the amputated limb at a distance spaced from the osseointegrated device.

21 Claims, 12 Drawing Sheets

(51) Int. Cl.
*A61F 2/70* (2006.01)
*A61F 2/72* (2006.01)
*A61L 27/12* (2006.01)
*A61F 2/78* (2006.01)

(52) U.S. Cl.
CPC ....... *A61L 27/12* (2013.01); *A61F 2002/7887* (2013.01); *A61L 2300/412* (2013.01)

(58) Field of Classification Search
USPC ............................................... 623/25, 34–37
See application file for complete search history.

(56) References Cited

U.S. PATENT DOCUMENTS

| | | | |
|---|---|---|---|
| 2007/0055383 A1* | 3/2007 | King | A61F 2/68 623/34 |
| 2007/0060891 A1* | 3/2007 | Skiera | A61F 2/2814 604/175 |
| 2009/0254196 A1* | 10/2009 | Cox | A61F 2/2814 623/33 |
| 2010/0106259 A1* | 4/2010 | Llinas | A61B 5/04001 623/25 |
| 2013/0123940 A1* | 5/2013 | Hurley | A61F 2/80 623/33 |
| 2016/0184112 A1* | 6/2016 | Radspieler | A61F 2/7812 623/36 |

FOREIGN PATENT DOCUMENTS

| | | |
|---|---|---|
| CN | 104053416 A | 9/2014 |
| EP | 2907484 A1 | 8/2015 |
| WO | 2012026870 A1 | 3/2012 |
| WO | 2013150298 A1 | 10/2013 |
| WO | 2014/015303 A1 | 1/2014 |
| WO | 2014015303 A1 | 1/2014 |
| WO | 2014040061 A1 | 3/2014 |

OTHER PUBLICATIONS

Combined Search and Examination Report dated Feb. 29, 2016, regarding GB Application No. GB1517134.1.
Combined Search and Examination Report dated May 15, 2019, regarding GB Application No. GB1810841.5.
International Search Report and Written Opinion dated Feb. 10, 2017, regarding PCT/GB2016/053010.
Further Examination Report dated Dec. 18, 2018, regarding UK Application No. GB1517134.1.
United Kingdom action before Search Report dated Dec. 19, 2018, regarding UK Application No. GB1810841.5.
The First Office Action and Search Report issued in Chinese Patent Application No. 201680067986.1, dated Sep. 29, 2019.
European examination report dated Jan. 30, 2020 for corresponding EP application No. 16777752.3.
Japanese Office Action with corresponding JP Application No. 2018-517200 dated Sep. 11, 2020.
Japanese Office Action with English translation received from corresponding JP Application No. 2018-517200 dated Apr. 27, 2021.
Chinese version of CN OA issued for CN Appl. No. 201680067986.1, dated Jul. 7, 2021, 5 pages.
English language translation of CN OA issued for CN. Appl. No. 201680067986.1, dated Jul. 7, 2021, 7 pages.
An English language abstract of CN Appl. No. 103519924A, 1 page.

* cited by examiner

MODULAR DEVICE AND INTERFACE DESIGN

TECHNICAL FIELD

The present invention relates to a prosthetic interface device. In particular, the present invention provides for an osseointegrated prosthetic interface device for permanent or semi-permanent fitting to the end of a patient's limb to enable attachment to any future prosthesis.

BACKGROUND

Amputations are commonly performed to save the remainder of limbs where damage or disease threatens the viability of the limb itself. It is believed that the rates of amputation is likely to increase as a result of the general increases in the rates of diabetes and obesity.

Traditionally with amputees, prosthetics are offered to address some of a patient's functional and/or aesthetic concerns. These prosthetics are often connectable to the amputated limbs by means of a cup/socket arrangement. Although often addressing the aesthetic concerns of a patient, as the coupling interface tends to be weak, functionally, these systems/devices tend to fail in providing patients with the strength needed for adequate functional use. Additionally, the interaction between the socket and stump is often a significant source of discomfort for the patient.

To address these deficiencies, the development of percutaneous osseointegrated interface devices has been developed to couple with the prosthesis. Although addressing the patient's need for improved functionality, these systems are prone to infection at the transcutaneous site.

To reduce this risk, some of these percutaneous osseointegrated prostheses systems have focussed on forming a seal between the skin of the limb and the implant. Although reducing the risk of infection, these systems have often failed to show long term skin-implant viability or demonstrable mechanical robustness.

Additionally, these systems have the major disadvantage of often requiring a patient to undergo multiple surgeries; for example, a patient will normally require a first surgery to create the stump; once this has healed, the patient will be fitted with a threaded bar into the bone; again, its only after this surgery has healed that a further surgery will be scheduled to fit a further bar, mateable with already implanted bar, which protrudes through the skin. It is not uncommon for multiple further corrective surgeries to also be required.

Therefore, there is a need for an improved prosthetic osseointegrated interface device which addresses the deficiencies in the current state of technology.

SUMMARY

In one embodiment, there is described an osseointegrated interface device for engagement with an amputated limb including the skin comprising: a cap portion engageable with an osseointegrated device; wherein the cap portion comprises a surrounding flange; wherein in use the surrounding flange receives the skin of the amputated limb at a distance spaced from the osseointegrated device.

Preferably, the device further comprises a stem portion engageable with the cap portion. The stem portion may comprise any one or more of a threaded section, a compression fitting, a bayonet or other suitable means for engaging with the cap portion. When in use, the stem portion may be osseointegrated. When in use the stem portion may be engageable with the osseointegrated device.

Preferably, the stem portion further comprises a prosthesis connector. The means for prosthesis connector may include female and male connection portions. The prosthesis connector may have a substantially triangular configuration. The prosthesis connector may comprise any one or more of a threaded section, a compression fitting, a bayonet or other suitable means for facilitating fixing of the connector to the means for prosthesis connection.

Preferably, the device further comprises one or more ports. The one or more ports may facilitate for one or more of the following: passage of biosensors; passage of cables carrying electrical data for control of a prosthesis when in use; access through which fluids or gasses can be passed either continuously, periodically or in a single instance; access for surgical procedures including keyhole surgery; and access for other medical procedures including but not limited to administering of medicines, draining of edema fluid in the stump or care of internal tissues.

Preferably, the device further comprises one or more cables or wires carrying electrical data for control of a prosthesis when in use. The one or more cables or wires may facilitate feedback from the prosthesis when in use. The one or more cables or wires may be connectable to nerve cuffs and/or muscle activation sensing electrodes and/or other electrical connections to or from the nervous system or other internal tissues comprising the data for control of the prosthesis. The electrical data may include neural and/or muscular data. The one or more cables or wires may comprise a shape, material and/or particular properties, mechanical or otherwise, which is biocompatible and preferably minimizes tissue reaction. The one or more cables or wires may be selected to minimize tissue damage caused from chemical reactions, toxicity or otherwise. The one or more cables or wires may comprise cuff, needle, sieve or micro array electrodes and/or implantable myoelectric sensors or similar. The one or more cables or wires in use may connect to the tissue of the limb without requiring passage through the bone. The one or more cables or wires in use may facilitate an electrical connection between the limb and prosthetic device connected thereto.

Preferably, the device further comprises an electronics unit to detect and/or process nerve signals. The processing may include neural processing for neural control and/or communication and/or patient health monitoring. The detection and/or processing may include any one or more of individual nerve and muscle activations; analysis of groups of muscles and nerves; dynamics of firing patterns of nerves or muscles including the timing of firing such as frequency, rate, interval, shape of firing signal and the distribution pattern across the population of neurons; and the overall changes in electrical potential of tissue at one or more sites anywhere within the amputee.

The distance between the surrounding flange and the osseointegrated device in use may be substantially the radius of the amputated limb. The distance between the surrounding flange and the osseointegrated device in use may be a portion of the radius of the amputated limb. The distance between the surrounding flange and the osseointegrated device may be such that in use the skin received by the flange is not in contact with the osseointegrated device.

Preferably, the surrounding flange may have dimensions which provide a homeostatic barrier about the amputated limb in use. The dimensions of the surrounding flange may be adaptable. The adaptable dimensions may include one or more of the angle that the flange protrudes in respect of the cap portion, the geometry of connection between the flange and the cap portion including but not limited to the curvature radii of the connection between the flange and the cap portion, the relative sizing of profile of the cross-section of the flange, the length of the flange and the thickness of the flange.

Preferably, the flange comprises a bio-compatible material. Additionally or alternatively, the cap portion may comprise a bio-compatible material. Additionally or alternatively, the device comprises a bio-compatible material. The bio-compatible material may comprise titanium, medically relevant titanium alloys including but not limited to Ti6Al4V, stainless steel, 316 stainless steel, high-density polyethylene (HDPE), polylactic acid (PLA), polypropylene (PP) or other medically relevant polymer or metal, and/or combinations or mixtures thereof. The bio-compatible material may comprise a biomimetic surface microstructure. The bio-compatible material may comprise porosity at surface.

The bio-compatible material may be an open-celled foam. The pore size may be in the range of 50 pm to 800 pm. The pore size may range from 100 pm to 750 pm, 150 pm to 700 pm, 200 pm to 650 um, 250 pm to 600 pm, 300 pm to 550 pm, 350 pm to 500 pm, 400 pm to 450 pm or any combined or intermediate range thereof. The pore size may range from 200 pm to 300 p.m. The pore size may or may not be uniform and/or the porosity may extend any part or substantially all of the flange, the cap portion and/or the device. The density of the pores may be no less than $1/mm^3$, and/or optionally, wherein density of the pores is inferred from and/or dependent on the size of the pores.

The pores may penetrate less than 1 mm into the surface of the flange, cap portion and/or device, less than 2 mm into the surface, less than 3 mm into the surface, less than 4 mm into the surface, less than 5 mm into the surface or any intermediate thereof. The pores may extend through substantially the full thickness of the flange. The pores penetrate 2 mm into the surface of the flange, cap portion and/or device.

Preferably, the flange further comprises one or more conduits for providing nutrient flow between the skin and the tissue of the amputated limb, for example the muscle. The conduits may extend through substantially the entire thickness of the flange. The conduits may be 850 pm, 900 pm, 950 pm, 1.05 mm, 1.1 mm, 1.15 mm, 1.2 mm, 1.25 mm or any dimension in between. The conduits may range from 800 pm to 1 mm.

Preferably, the angle that the flange protrudes in respect of the cap portion is at or less than 90 deg, at or less than 80 deg, at or less than 70 deg, at or less than 60 deg, at or less than 50 deg, at or less than 40 deg, at or less than 30 deg, at or less than 20 deg, at or less than 10 deg or any intermediate thereof. The angle that the flange protrudes in respect of the cap portion may be at 45 degrees.

Preferably, the length of the flange is 5 mm, 10 mm, 20 mm, 25 mm, 30 mm to 35 mm or any intermediate thereof. The length of the flange may be 15 mm.

Preferably, the thickness of the flange is less than 1 mm, less than 2 mm, less than 3 mm, less than 4 mm to less than 5 mm or any intermediate thereof. The thickness of the flange may be 3 mm.

Preferably, the geometry of the connection where the flange meets the cap portion is substantially concave, and optionally, substantially curved, circular or parabola-like. The geometry may comprise a radius of curvature where the flange meets the cap portion at 1 mm, 2 mm, 3 mm, 4 mm, 6 mm, 7 mm, 8 mm, 9 mm, 10 mm or any intermediate thereof. The radius of the curvature where the flange meets the cap portion may be 5 mm.

Preferably, the flange further comprises hydroxyapatite and/or any other material which promotes growth and/or integration of tissue groups. The flange may be constructed by wire sintering or similar. The flange may be constructed by bead sintering. The flange may be constructed by 3D printing. The flange may be constructed by chemical etching. The flange may be constructed by metal casting with void creating materials.

In a further aspect of the invention, there is described a method of manufacturing and/or fitting the device of any preceding claim, the method comprising: adapting any one or more of the dimensions of the surrounding flange in view of the amputated limb.

Preferably the method further comprises selecting one or more of the following parameters of the flange: surface properties including stiffness and surface tension, the mean asperity sizes, overall density and solid and/or fluid permeabilities.

In an additional or alternative aspect of the invention, there is described a method of fitting the osseointegrated interface device of any preceding claim to an osseointegrated device.

In a further embodiment, there is described a device for engagement with an amputated limb including the skin comprising: a cap portion comprising a surrounding flange for engagement with the skin of the amputated limb; wherein the dimensions of the surrounding flange provide a homeostatic barrier about the amputated limb in use.

Preferably, the dimensions of the surrounding flange are adaptable. The adaptable dimensions may include one or more of the angle that the flange protrudes in respect of the cap portion, the geometry of connection between the flange and the cap portion including but not limited to the curvature radii of the connection between the flange and the cap portion, the relative sizing of profile of the cross-section of the flange, the length of the flange and the thickness of the flange.

Preferably, the flange comprises a bio-compatible material. The cap portion may comprise a bio-compatible material. The device may comprise a bio-compatible material. The bio-compatible material may comprise titanium, medically relevant titanium alloys including but not limited to Ti6Al4V, stainless steel, 316 stainless steel, high-density polyethylene (HDPE), polylactic acid (PLA), polypropylene (PP) or other medically relevant polymer or metal, and/or combinations or mixtures thereof. The bio-compatible material may comprise a biomimetic surface microstructure. The bio-compatible material may comprise porosity at surface.

Preferably, the bio-compatible material is a open-celled foam. The pore size may be in the range of 50 p.m to 800 p.m. The pore size ranges may be from 100 p.m to 750 p.m, 150 p.m to 700 p.m, 200 p.m to 650 p.m, 250 p.m to 600 p.m, 300 p.m to 550 p.m, 350 p.m to 500 p.m, 400 p.m to 450 p.m or any combined or intermediate range thereof. The pore size may range from 200 p.m to 300 p.m. The pore size may or may not be uniform and/or the porosity may extend any part or substantially all of the flange, the cap portion and/or the device. The density of the pores may be no less than $1/mm^3$, and/or optionally, wherein density of the pores is inferred from and/or dependent on the size of the pores.

The pores may penetrate less than 1 mm into the surface of the flange, cap portion and/or device, less than 2 mm into the surface, less than 3 mm into the surface, less than 4 mm into the surface, less than 5 mm into the surface or any intermediate thereof. The pores may extend through substantially the full thickness of the flange. The pores may penetrate 2 mm into the surface of the flange, cap portion and/or device.

Preferably, the flange may further comprise one or more conduits for providing nutrient flow between the skin and the tissue of the amputated limb, for example the muscle. The conduits may extend through substantially the entire thickness of the flange. The conduits may be 850 p.m, 900 p.m, 950 p.m, 1.05 mm, 1.1 mm, 1.15 mm, 1.2 mm, 1.25 mm or any dimension in between. The conduits may range from 800 um to 1 mm.

Preferably, the angle that the flange protrudes in respect of the cap portion is at or less than 90 deg, at or less than 80 deg, at or less than 70 deg, at or less than 60 deg, at or less than 50 deg, at or less than 40 deg, at or less than 30 deg, at or less than 20 deg, at or less than 10 deg or any intermediate thereof. The angle that the flange protrudes in respect of the cap portion is at 45 degrees.

Preferably, the length of the flange is 5 mm, 10 mm, 20 mm, 25 mm, 30 mm to 35 mm or any intermediate thereof. The length of the flange may be 15 mm.

Preferably, the thickness of the flange is less than 1 mm, less than 2 mm, less than 3 mm, less than 4 mm to less than 5 mm or any intermediate thereof. The thickness of the flange may be 3 mm.

Preferably, the geometry of the connection where the flange meets the cap portion is substantially concave, and optionally, substantially curved, circular or parabola-like.

The geometry comprises a radius of curvature where the flange meets the cap portion may be at 1 mm, 2 mm, 3 mm, 4 mm, 6 mm, 7 mm, 8 mm, 9 mm, 10 mm or any intermediate thereof. he radius of the curvature where the flange meets the cap portion may be 5 mm.

Preferably, the flange further comprises hydroxyapatite and/or any other material which promotes growth and/or integration of tissue groups.

Preferably, the flange is constructed by wire sintering or similar. Additionally or alternatively, the flange may be constructed by bead sintering. Additionally or alternatively, the flange may be constructed by 3D printing. Additionally or alternatively, the flange may be constructed by chemical etching. Additionally or alternatively, the flange may be constructed by metal casting with void creating materials.

Preferably, the device is engageable with the amputated limb via an osseointegrated device.

Preferably, the device further comprises a stem portion engageable with the cap portion. The stem portion may comprise any one or more of a threaded section, a compression fitting, a bayonet or other suitable means for engaging with the cap portion. When in use the stem portion may be osseointegrated. When in use the stem portion may be engageable with an osseointegrated device.

Preferably, the stem portion further comprising a prosthesis connector. The means for prosthesis connector may include female and male connection portions. The prosthesis connector may have a substantially triangular configuration. The prosthesis connector may comprise any one or more of a threaded section, a compression fitting, a bayonet or other suitable means for facilitating fixing of the connector to the means for prosthesis connection.

Preferably, the device further comprises one or more ports. The one or more ports may facilitate for one or more of the following: passage of biosensors; passage of cables carrying electrical data for control of a prosthesis when in use; access through which fluids or gasses can be passed either continuously, periodically or in a single instance; access for surgical procedures including keyhole surgery; and access for other medical procedures including but not limited to administering of medicines, draining of edema fluid in the stump or care of internal tissues.

Preferably, the device further comprises one or more cables or wires carrying electrical data for control of a prosthesis when in use. The one or more cables or wires may facilitate feedback from the prosthesis when in use. The one or more cables or wires may be connectable to nerve cuffs and/or muscle activation sensing electrodes and/or other electrical connections to or from the nervous system or other internal tissues comprising the data for control of the prosthesis. The electrical data may include neural and/or muscular data. The one or more cables or wires may comprise a shape, material and/or particular properties, mechanical or otherwise, which may be biocompatible and preferably may minimize tissue reaction. The one or more cables or wires may be selected to minimize tissue damage caused from chemical reactions, toxicity or otherwise. The one or more cables or wires may comprise cuff, needle, sieve or micro array electrodes and/or implantable myoelectric sensors or similar.

The one or more cables or wires in use may connect to the tissue of the limb without requiring passage through the bone. The one or more cables or wires in use may facilitate an electrical connection between the limb and prosthetic device connected thereto.

Preferably, the device further comprises an electronics unit to detect and/or process nerve signals. The processing may include neural processing for neural control and/or communication and/or patient health monitoring. The detection and/or processing may include any one or more of individual nerve and muscle activations; analysis of groups of muscles and nerves; dynamics of firing patterns of nerves or muscles including the timing of firing such as frequency, rate, interval, shape of firing signal and the distribution pattern across the population of neurons; and the overall changes in electrical potential of tissue at one or more sites anywhere within the amputee.

In a further embodiment, there is described an interface device for engagement with skin, the device comprising: a cap portion; wherein the cap portion comprises a surrounding flange engageable with the skin; and wherein the cap portion comprises one or more ports for transcutaneous access.

In a further embodiment, there is an osseointegrated interface device for engagement with an amputated limb comprising: a cap portion engageable with an osseointegrated device via a stem portion; wherein the stem portion is further engageable with a prosthesis connector.

In a further embodiment, there is described a device for engagement with the skin, the device comprising: a cap portion for engagement with the skin; and an electronics unit to detect and/or process nerve signals.

Preferably, the device further comprises a stem portion engageable with the cap portion. The stem portion may comprise any one or more of a threaded section, a compression fitting, a bayonet or other suitable means for engaging with the cap portion. When in use, the stem portion may be osseointegrated. When in use the stem portion may be engageable with the osseointegrated device.

Preferably, the stem portion further comprises a prosthesis connector. The means for prosthesis connector may include female and male connection portions. The prosthesis connector may have a substantially triangular configuration. The prosthesis connector may comprise any one or more of a threaded section, a compression fitting, a bayonet or other suitable means for facilitating fixing of the connector to the means for prosthesis connection.

Preferably, the device further comprises one or more ports. The one or more ports may facilitate for one or more of the following: passage of biosensors; passage of cables carrying electrical data for control of a prosthesis when in use; access through which fluids or gasses can be passed either continuously, periodically or in a single instance; access for surgical procedures including keyhole surgery; and access for other medical procedures including but not limited to administering of medicines, draining of edema fluid in the stump or care of internal tissues.

Preferably, the device further comprises one or more cables or wires carrying electrical data for control of a prosthesis when in use. The one or more cables or wires may facilitate feedback from the prosthesis when in use. The one or more cables or wires may be connectable to nerve cuffs and/or muscle activation sensing electrodes and/or other electrical connections to or from the nervous system or other internal tissues comprising the data for control of the prosthesis. The electrical data may include neural and/or muscular data. The one or more cables or wires may comprise a shape, material and/or particular properties, mechanical or otherwise, which is biocompatible and preferably minimizes tissue reaction. The one or more cables or wires may be selected to minimize tissue damage caused from chemical reactions, toxicity or otherwise. The one or more cables or wires may comprise cuff, needle, sieve or micro array electrodes and/or implantable myoelectric sensors or similar. The one or more cables or wires in use may connect to the tissue of the limb without requiring passage through the bone. The one or more cables or wires in use may facilitate an electrical connection between the limb and prosthetic device connected thereto.

Preferably, the device further comprises an electronics unit to detect and/or process nerve signals. The processing may include neural processing for neural control and/or communication and/or patient health monitoring. The detection and/or processing may include any one or more of individual nerve and muscle activations; analysis of groups of muscles and nerves; dynamics of firing patterns of nerves or muscles including the timing of firing such as frequency, rate, interval, shape of firing signal and the distribution pattern across the population of neurons; and the overall changes in electrical potential of tissue at one or more sites anywhere within the amputee.

The distance between the surrounding flange and the osseointegrated device in use may be substantially the radius of the amputated limb. The distance between the surrounding flange and the osseointegrated device in use may be a portion of the radius of the amputated limb. The distance between the surrounding flange and the osseointegrated device may be such that in use the skin received by the flange is not in contact with the osseointegrated device.

Preferably, the surrounding flange may have dimensions which provide a homeostatic barrier about the amputated limb in use. The dimensions of the surrounding flange may be adaptable. The adaptable dimensions may include one or more of the angle that the flange protrudes in respect of the cap portion, the geometry of connection between the flange and the cap portion including but not limited to the curvature radii of the connection between the flange and the cap portion, the relative sizing of profile of the cross-section of the flange, the length of the flange and the thickness of the flange.

Preferably, the flange comprises a bio-compatible material. Additionally or alternatively, the cap portion may comprise a bio-compatible material. Additionally or alternatively, the device comprises a bio-compatible material. The bio-compatible material may comprise titanium, medically relevant titanium alloys including but not limited to Ti6Al4V, stainless steel, 316 stainless steel, high-density polyethylene (HDPE), polylactic acid (PLA), polypropylene (PP) or other medically relevant polymer or metal, and/or combinations or mixtures thereof. The bio-compatible material may comprise a biomimetic surface microstructure. The bio-compatible material may comprise porosity at surface.

The bio-compatible material may be an open-celled foam. The pore size may be in the range of 50 pm to 800 pm. The pore size may range from 100 pm to 750 pm, 150 pm to 700 pm, 200 pm to 650 um, 250 pm to 600 pm, 300 pm to 550 pm, 350 pm to 500 pm, 400 pm to 450 pm or any combined or intermediate range thereof. The pore size may range from 200 pm to 300 p.m. The pore size may or may not be uniform and/or the porosity may extend any part or substantially all of the flange, the cap portion and/or the device. The density of the pores may be no less than $1/mm^3$, and/or optionally, wherein density of the pores is inferred from and/or dependent on the size of the pores.

The pores may penetrate less than 1 mm into the surface of the flange, cap portion and/or device, less than 2 mm into the surface, less than 3 mm into the surface, less than 4 mm into the surface, less than 5 mm into the surface or any intermediate thereof. The pores may extend through substantially the full thickness of the flange. The pores penetrate 2 mm into the surface of the flange, cap portion and/or device.

Preferably, the flange further comprises one or more conduits for providing nutrient flow between the skin and the tissue of the amputated limb, for example the muscle. The conduits may extend through substantially the entire thickness of the flange. The conduits may be 850 pm, 900 pm, 950 pm, 1.05 mm, 1.1 mm, 1.15 mm, 1.2 mm, 1.25 mm or any dimension in between. The conduits may range from 800 pm to 1 mm.

Preferably, the angle that the flange protrudes in respect of the cap portion is at or less than 90 deg, at or less than 80 deg, at or less than 70 deg, at or less than 60 deg, at or less than 50 deg, at or less than 40 deg, at or less than 30 deg, at or less than 20 deg, at or less than 10 deg or any intermediate thereof. The angle that the flange protrudes in respect of the cap portion may be at 45 degrees.

Preferably, the length of the flange is 5 mm, 10 mm, 20 mm, 25 mm, 30 mm to 35 mm or any intermediate thereof. The length of the flange may be 15 mm.

Preferably, the thickness of the flange is less than 1 mm, less than 2 mm, less than 3 mm, less than 4 mm to less than 5 mm or any intermediate thereof. The thickness of the flange may be 3 mm.

Preferably, the geometry of the connection where the flange meets the cap portion is substantially concave, and optionally, substantially curved, circular or parabola-like. The geometry may comprise a radius of curvature where the flange meets the cap portion at 1 mm, 2 mm, 3 mm, 4 mm, 6 mm, 7 mm, 8 mm, 9 mm, 10 mm or any intermediate thereof. The radius of the curvature where the flange meets the cap portion may be 5 mm.

Preferably, the flange further comprises hydroxyapatite and/or any other material which promotes growth and/or integration of tissue groups. The flange may be constructed by wire sintering or similar. The flange may be constructed by bead sintering. The flange may be constructed by 3D printing. The flange may be constructed by chemical etching. The flange may be constructed by metal casting with void creating materials.

The features of each of the above aspects and/or embodiments may be combined as appropriate, as would be apparent to the skilled person, and may be combined with any of the aspects of the invention. Indeed, the order of the embodiments and the ordering and location of the preferable features is indicative only and has no bearing on the features themselves. It is intended for each of the preferable and/or optional features to be interchangeable and/or combinable with not only all of the aspect and embodiments, but also each of preferable features.

BRIEF DESCRIPTION OF DRAWINGS

For better understanding of the aspects and/or embodiments described herein and to show how the same may be carried into effect, reference will now be made, by way of example only, to the accompanying figures, in which.

Figure 1A:
FIG. 1A is a photograph of an amputated limb without and/or before a prosthetic interface device according to one embodiment is fitted thereto.

It will be appreciated that although features from each of the embodiments may be identified by different reference numerals in the figures and throughout the description, similar features including the properties and functionality attributed thereto from one embodiment may be interchangeable with those of another embodiment.

DETAILED DESCRIPTION

References will now be made in detail to the various aspects and/or embodiments, examples of which are illustrated in the accompanying figures. In the following detailed description, numerous specific details are set forth in order to provide a thorough understanding of the invention. However, it will be apparent to one of ordinary skill in the art that the invention may be practiced without these specific details and/or with any number of the specifics from one or more of the embodiments unless description to the contrary has been noted herein.

Figure 1B:
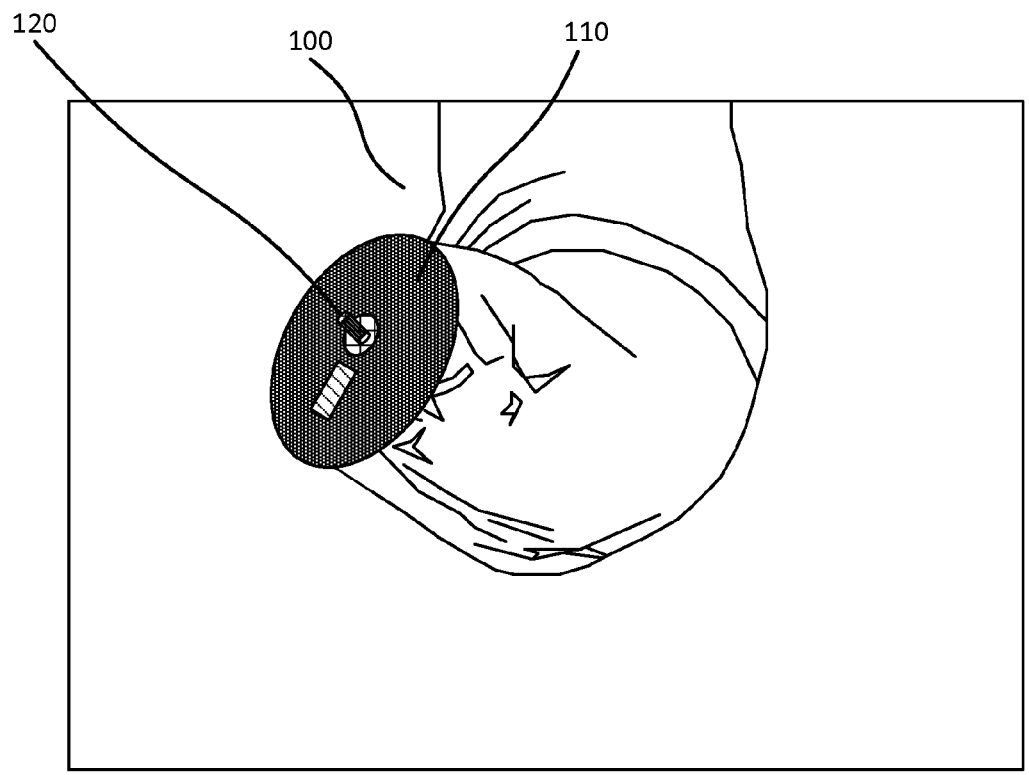
FIG. 1B is a photograph of the amputated limb of FIG. 1A with a prosthetic interface device according to one embodiment fitted thereto.

FIGS. 1A and 1B are photographs of an amputated limb without and/or before and after a prosthetic interface device has been fitted thereto, respectively. The terms "prosthesis" and "prosthetic" are used throughout and should be broadly construed to include any device designed to replace a missing or damaged part of the body or to make a part of the body work better and includes, but is not limited to, bionic limbs and similar. Additionally, the terms "patient" and "amputee" should be broadly construed to include both human and animal subjects.

The prosthetic interface device 100 in this embodiment is a bone implanted (osseointegrated) prosthetic interface device. Although not required or essential, in a preferred embodiment, the patient will be fitted with prosthetic interface device 100 during amputation instead of having a stump formed. However, it is envisaged that retroactive fitting of prosthetic interface device 100 once a stump has formed can also occur, as depicted in FIG. 1A.

Advantageously, the prosthetic interface device 100 in this embodiment, provides mechanical, neural and soft tissue integration with the amputated limb. It will be appreciated that although the prosthetic interface device 100 in this embodiment provides neural integration, this feature is not essential but rather preferable in some embodiments.

Once the prosthetic interface device 100 has been fitted to the limb, a prosthesis can be connected thereto. Although in this embodiment the surface 110 of prosthetic interface device 100 is relatively flat and uniformly round, i.e. disc shaped, and covers substantially the entire area of the limb, it will be appreciated that prosthetic interface device 100 need not have this shape or configuration as will be discussed in more detail below.

Embodiments of the invention include the skin interface device at the full width or partial width of the amputated limb. It has been found that where the prosthetic interface device 100 is substantially the full surface area of the amputated limb, the surgery made easier. However, it has also been found that where the prosthetic interface device 100 has a surface area less than that of the amputated limb, there is less residing of the muscles and any cauterized vessels, for example caused from tissue swelling during/after surgery.

The prosthetic interface device 100 may be designed to cover any amount of the area of the amputated limb; for example, a particular percentage of the limb. Also, it will be appreciated that not all amputated limbs have the same dimensions and shapes. As such, in certain preferred embodiments, the dimensions of prosthetic interface device 100 may be configurable or adaptable to suit the particular type of limb (e.g. lower leg v. forearm etc.) and/or may be customizable depending on the specifications of the particular patient. For example, the surface 110 of the prosthetic interface device 100 may not comprise a disk shape, but instead may comprise a (substantially or semi) conical, (substantially or semi) oblong or any other desired configuration, more detail of which is described below, for example with respect to FIGS. 9A to 9D. Furthermore, the cap in FIGS. 9A to 9D may or may not be rotationally symmetric, particularly when engaging with limb locations featuring substantially off-center main bones.

Figure 2A:
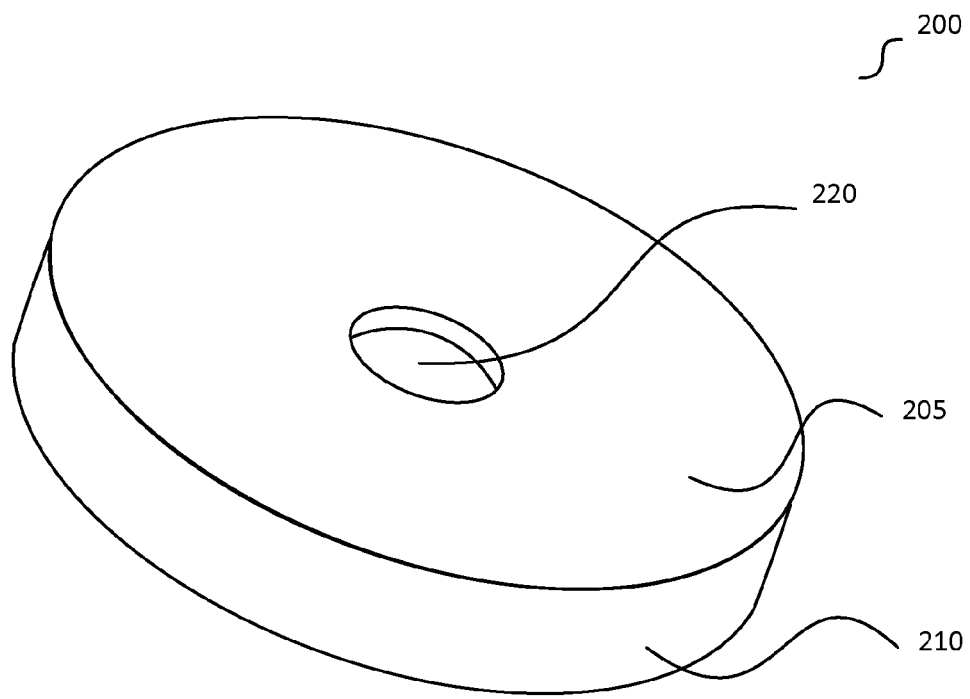
FIG. 2A depicts a top view of the cap portion of the prosthetic interface device according to one embodiment.
Figure 2B:
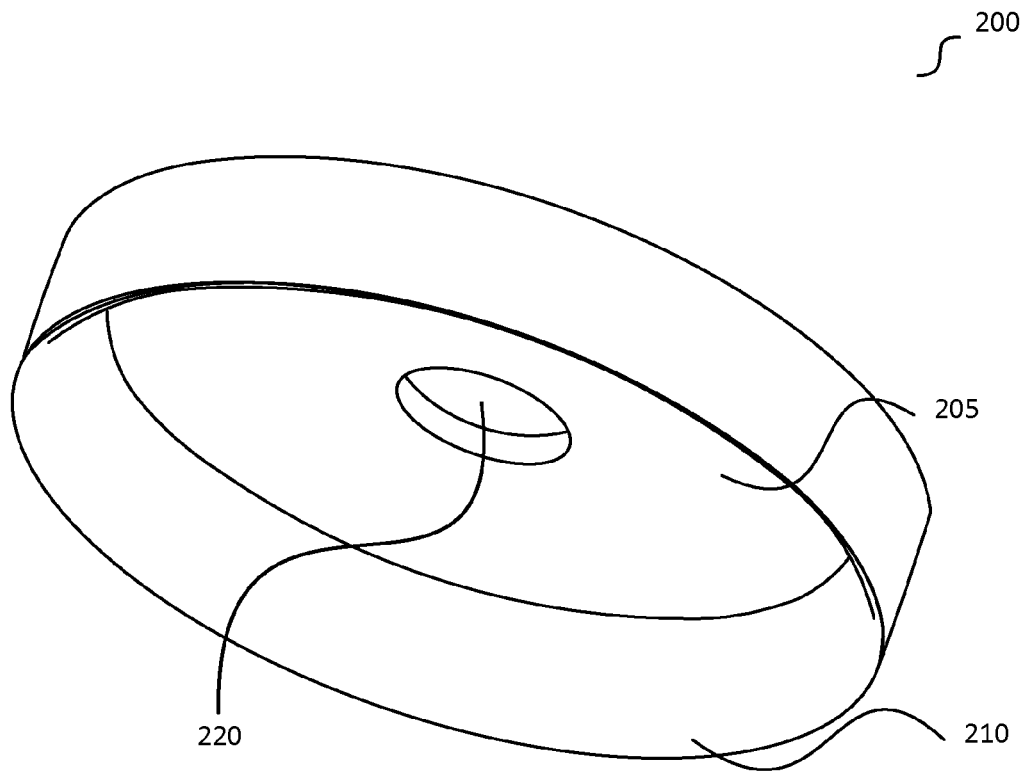
FIG. 2B depicts a bottom view of the cap portion of the prosthetic interface device of FIG. 2A.

Prosthetic interface device 100 may comprise a means 120 for facilitating connection (e.g. means adaptable for connection with a prosthesis connector), as will be described in more detail below, for example with respect to FIG. 5; wherein the prosthesis connector may be adaptable such that its shape and/or dimensions are engageable with specific prostheses. For example, a particular patient may have a desire for a particular prostheses type, the dimensions of prosthetic interface device 100 may be determined based on those ideal for maximum compatibility with the particular prosthesis. In some preferred embodiments, a connector is designed to be a universal connector and hence engage with all possible prostheses FIGS. 2A and 2B depict a top and bottom view of a cap portion of the prosthetic interface device 100 according to one embodiment.

The cap portion 200 is the housing portion of the prosthetic interface device 100 which is configurable to house or cover a portion or all of the surface area of the end of the amputee's limb. In this embodiment, the cap portion 200 comprises a surface 205, in this example having a circular disk shape, with a surrounding flange 210.

In some embodiments, the cap portion 200 comprises a flexible material, for example, but not limited to a polymer which may or may not be coated.

When in use, it is envisaged that the cap portion 200 will be secured to a stem portion (not shown, but described in respect of FIG. 3) which may be osseointegrated or connected to an osseointegrated device through an aperture 220 in the surface 205 of the cap 200 and that the edges of the surrounding flange 210 of the cap portion 200 will interface with the skin of the amputated limb. As mentioned above, the detailed shape and the dimensions of each of the component parts of the cap portion 200 are exemplary only. Indeed, any desired configuration may be provided, more detail of which is described below, for example with respect to FIGS. 9A to 9D. Indeed, alternative embodiments may include the flange 210 protruding downwards from the side of the surface 205 at any angle to the cap. The flange 210 may be integral with the surface 205 of the cap 200 or may be distinct from but fixable thereto.

In one exemplary embodiment of the prosthetic interface device 100, the surface 205 of the cap portion 200 protrudes 2 cm from the circumference of the aperture 220 which may be configurable to receive a (osseointegrated) stem portion. In this exemplary embodiment, after the protrusion of the surface 205 for 2 cm, surrounding flange 210 may extend further (from the circumference of the aperture), for example, where the flange 210 is an angled flange. It will be appreciated that when in use, the flange 210, angled or not, will be substantially provided within the interior of the stump or limb as it is intended to interface with the skin of the amputated limb.

Although in the above exemplary embodiment an aperture 220 is provided, no aperture 220 is required. Indeed, in additional or alternative embodiments, an integrated or distinct connection means can be provided to facilitate mechanical connection between cap portion 200 and the limb, and preferably via an osseointegrated stem portion.

Although in the above exemplary embodiment, the radius of the surface area of the surface 205 need can be any dimension which covered as large a radius as the amputated limb in question.

Not wishing to be bound by theory, it is believed that the larger the surface area of the cap portion 200, the less chance of infection from the wound site, around the skin integration area where the flange 210 adjoins the skin of the amputated limb, spreading to the bone via the osseointegrated device; i.e. the more distance between these two features the less chance of infection spreading. Therefore, in one preferred embodiment, the radius of the cap portion 200 is not less than 1 cm and/or the surface area of the cap portion 200 is no less that 10% of the surface area of the amputated limb. However, it will be appreciated that the surface area of the cap portion 200 may be up to 20%, 30%, 40%, 50%, 60%, 70%, 80%, 90%, or 100% of the surface area of the amputated limb or any percentage therein between.

Again, not wishing to be bound by theory, it is believed that although there are advantages in providing as large a surface area of the cap portion 200 as possible in respect of the surface area of the amputated limb (for example, to provide distance between the skin integration site and any osseointegrated stem portion), there may be medical challenges in integrating the cap portion 200 to the amputated limb, specifically the surrounding flange 210 with the skin of the limb where the surface area of the limb is too close to the surface area of the amputated limb.

The cap portion 200 may comprise titanium, 316 stainless steel, high-density polyethylene (HDPE), polylactic acid (PLA), polypropylene (pp) or other FDA-approved polymer or metal, and/or combinations or mixtures thereof. In one exemplary embodiment, the cap portion 200 comprises a titanium alloy, optionally a grade 5 alloy such as Ti6Al4V, and could be either 3D printed or machined. Alternative materials include but is not limited to stainless steel (and its derivatives), for example having SAE grade 316.

As mentioned above, the surface 205 and surrounding flange 210 of the prosthetic interface device 100 may be adaptable such that it corresponds to the limb of an amputee. Indeed, in one embodiment, the cap portion 200 is manufactured specifically for a particular amputee such that it is specifically matching to their body geometry. In some preferable embodiments, the cap portion 200 may be manufactured by 3D printing.

Preferably, the prosthetic interface device 100 consists of a bio-compatible material. It will be appreciated that it is not essential for the entirety of the prosthetic interface device 100 or the cap portion 200 to consist of a bio-compatible material, but rather it is preferable for any edges and/or surfaces in contact with the skin, vascular or muscular tissue of the amputee to consist thereof. As such, in some embodiments only the surrounding flange 210 or a part thereof and/or the inner surface of the cap portion 200 (i.e. the side of surface 205 facing the limb) comprise the bio-compatible material, e.g. only parts of the cap portion 200 in contact with biological tissue will comprise bio-compatible materials. For example, the flange 210 (or any part there of) and/or a part(s) of the cap portion 200 may comprise titanium (alloys thereof including Ti6Al4V), stainless steel (and its derivatives), for example having SAE grade 316, high-density polyethylene (HDPE), polylactic acid (PLA), polypropylene (PP) or other FDA-approved polymer or metal, and/or combinations or mixtures thereof.

The biocompatible material of any portion of cap portion 200 (including or solely flange 210) may comprise a biomimetic surface microstructure as will be described in more detail below. In one additional or alternative embodiment, the material may include porosity at surface, open-celled foam bulk structure, possibility of through-surface pores. Pore sizes may be in the range of 50 p.m to 800 p.m. It will appreciated that the pore size may or may not be uniform and/or the porosity may extend any part or substantially all of the flange 210 and/or cap portion 200. In some embodiments, the pore sizes range from 100 pm to 750 pm, 150 pm to 700 pm, 200 pm to 650 pm, 250 pm to 600 pm, 300 pm to 550 pm, 350 pm to 500 pm, 400 p.m to 450 p.m or any combined or intermediate range thereof.

Not wishing to be bound by theory, it is believed that below the lower limit of 50 pm, cells that penetrate are unlikely to survive due to restricted space and lack of nutrients, and above the upper limit of 800 p.m the strength of the mechanical junction may decrease. In one embodiment, the flange 210 (and/or any portion(s) or surface of the cap portion 200) may be designed to be porous through substantially its full thickness with the open cell structure.

In additional or alternative embodiments, the flange 210 (and/or any portion or surface of the cap portion 200) may comprise one or more conduits designed to penetrate the full thickness alone in order to further aid fluid/nutrient transfer across the flange 210 (and/or any portion or surface of the cap portion 200) to the dermal tissues (or other biological tissue).

Preferably, the geometry of the edge/flange 210 of the cap portion 200 may be designed to promote soft tissue ingrowth, soft tissue adherence and to minimise stress concentrations (and maximize interface strength) at the skin/device interface when in use (it is also preferably designed to allow long term nutrient supply to the tissues on the outside of the flange 210 so they can maintain long term health).

Preferably, the edge/flange 210 of the cap portion 200 may be designed to allow the patient's skin to grow into them and thus maintain the homeostatic barrier between internal and external surfaces of the body that is normally provided by the skin. Preferably, this surface design comprise a pore size between 200-300 pm which, although not wishing to be bound by theory, is based on field wide tissue engineering knowledge of the acceptable range of pore sizes that are viable for cell health. The geometry of the surface design is preferably based on the bone tendon junction occurring at the supraspinatus tendon insertion site. In one exemplary embodiment, the edge/flange 210 comprises a skin compatible surface which may contain pores of the appropriate size further defined herein (for example 200 p.m), and a density with a lower bound pore density of 1/mm$^3$ and an upper bound inferred by the pore size.

Figure 3:
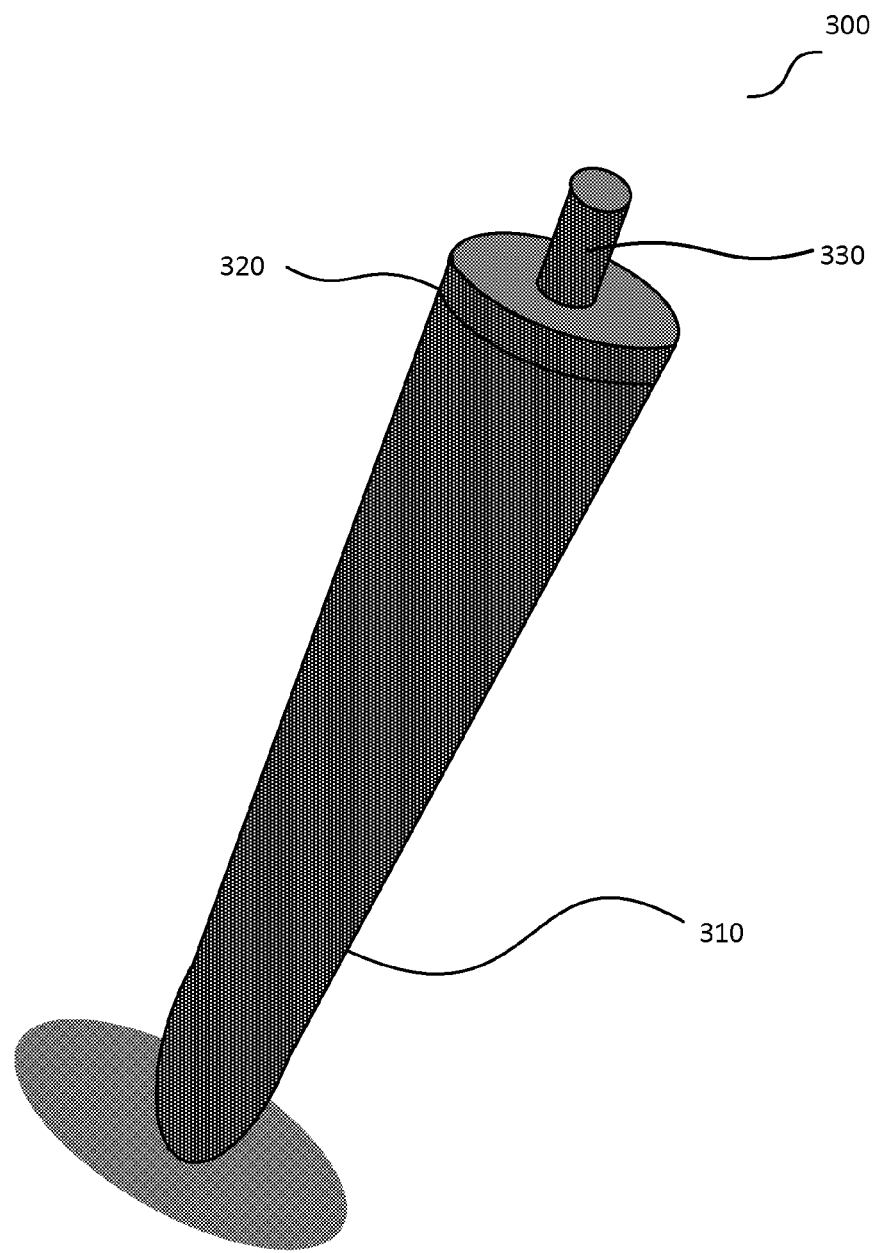
FIG. 3 illustrates a side view of the stem portion of the prosthetic interface device according to one embodiment, which is suitable for engagement firstly with the cap portion of FIGS. 2A and 2B and secondly with the prosthetic connector, for example the one depicted in FIG. 5.

FIG. 3 illustrates a side view of a stem portion of the prosthetic interface device 100 according to one embodiment, which is suitable for engagement with the cap portion 200 of FIGS. 2A and 2B and additionally with a prosthetic connector.

The prosthetic interface device 100 is intended to transmit biomechanical loads from a prosthetic limb into the skeletal system of the patient. In one embodiment, this will be achieved using one or more bone implants that will form the centre of the prosthetic interface device 100 and will pass through the cap portion 200, specifically aperture 220, as one piece. It will be appreciated that alternative arrangements can be provided. For example, the stem portion need not pass through the cap portion 200, but could be connectable there with by some means of connection, for example via some snap-to-lock or threaded screw arrangement or via used of an adhesive. It will be appreciated that the means for connection may comprise any known arrangement and may be integral to or distinct but additional to the disclosed arrangement.

In one embodiment the stem portion 300 comprises a titanium bone implant. However, it will be appreciated that any one or more bone implants can be used and any other material or composition fit for purpose may be used. It will also be appreciated that the stem portion 300 may comprise one or more portions.

In alternative embodiments, the bone implant can comprise stainless steel, for example 316 stainless steel, or any other material or composition suitable for being implanted in the bone. The stem portion 300 may further comprise surface coating and may be manufactured in accordance with the state of the art bone integration technology available commercially now or in the future which allows bone integration into the implant.

When in use, an inner portion 310 of the stem portion 300 may be surgically implanted into the limb of a patient. The inner portion 310 in this embodiment has a tapered wall; however, it will be appreciated that any size and shape which facilitates stable bone integration can be used including arrangements having additional radial or longitudinal ridges or grooves of any size. Indeed, it will be appreciated that the stem portion can be manufactured, having the composition and dimensions, in accordance with the state of the art bone implant technology available commercially now or in the future.

The outer portion 320 of the stem portion 300, which is on an edge opposed to the inner portion, comprises a protruding bar portion 330 that is engageable with cap portion 200 and the prosthetic connector. For example, the bar 330 may be configured such that it directly engages to cap portion 200 and additionally a prosthetic connector which may be adaptable to engage with a particular type of or particular prosthesis, for example in a plug-and-play or key-and-lock attachment manner. In one exemplary embodiment, the top of the bar portion 330 of the stem 300, and/or one or more portions thereof, may comprise a threaded section, compression fitting, bayonet or otherwise to allow for attachment with the prosthetic connector and/or cap portion 200.

Although the protruding bar portion 330 is described herein as a bar, it will be appreciated that it need not be a bar or a male connection. Any suitable means configurable or adaptable to connect to the cap portion and a prosthetic connector can be used.

The prosthetic connector may be a universal connector for attachment by any prostheses and may include but is not constrained by a neural connector. In one preferable embodiment, the bar 330 may comprise two threaded bars, however, it will be appreciated that any means suitable for engaging with the cap portion 200 and the prosthetic connector separately or in unison may be provided.

By providing an osseointegrated stem portion 300, the prosthetic interface device 100 is provided with a direct connection to the skeleton, bypassing the soft tissue and reducing the risk of sores often resulting from excessive force of the prosthesis on the skin of the limb. Further, unlike prostheses which are attached to an amputated limb via an osseointegrated interface device, the present prosthetic interface device 100 provides a better mechanical interface between the skin and the device by providing cap portion 200 reducing risk of separation and subsequent infection.

Figure 4:
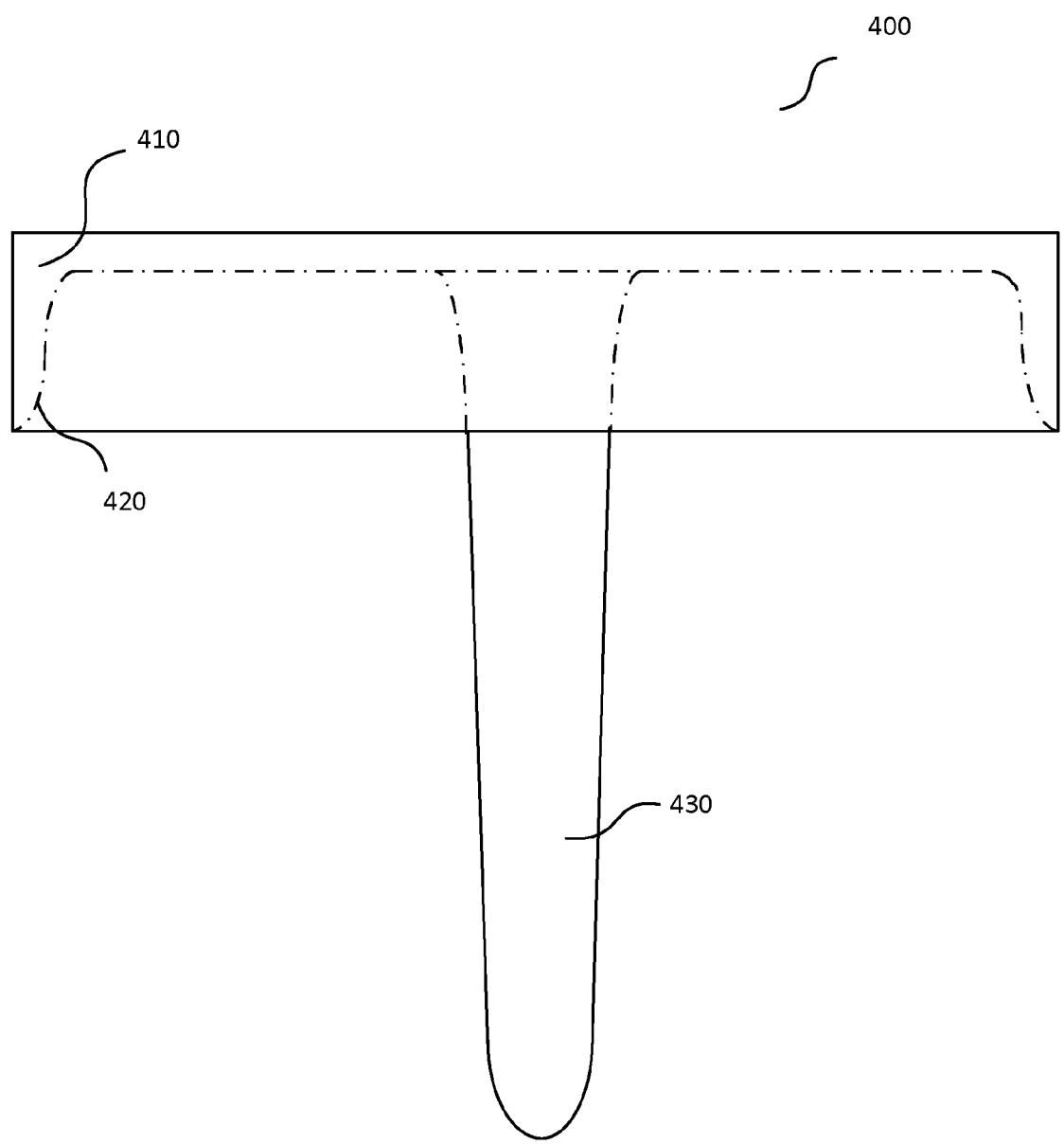
FIG. 4 depicts a cross-sectional side view of the prosthetic interface device according to one embodiment.

FIG. 4 depicts a cross-sectional side view of the prosthetic interface device according to one embodiment. The prosthetic interface device 400 is comparable to prosthetic interface device 100 and therefore features of these embodiments (and following ones) should be considered to be additional and/or interchangeable. The prosthetic interface device 400 comprises a surface 410 with a surrounding flange 420. The surrounding flange 420 may comprise a biocompatible material that allows the skin to interface with the prosthetic interface device 400; for example, any of the biocompatible materials detailed above in respect of FIGS. 2 and/or 3 may be used in respect thereof.

The prosthetic interface device 400 in this embodiment further comprises a stem portion 430 (comparable to stem portion 300) that in use is inserted into the bone to transmit biomechanical loads. It will be appreciated that the stem portion 430 may be integral with or simply connectable to surface portion 410. It will also be appreciated that although the stem portion 430 may be insertable into the bone, it may in alternative embodiment be connectable to an already inserted osseointegrated device.

The surrounding flange 420 allows the skin to interface with the prosthetic interface device 400 and may comprise the materials and have the configuration described in respect of surrounding flange/edge 210.

The prosthetic interface device 400 aims to utilise the osseointegrated connector or stem portion 430, which may comprise one or more parts, and a skin-integrated cap portion 200 or 410 engageable therewith and having a flange 420 to affix to an amputated limb, specifically to the skin of the limb. In use, the biological tissue of the amputated limb will abut the inner surface of the cap portion 200 with the flange 210, 420 adjoining the skin. Although multiple references have been provided for similar features of the various embodiments in this paragraph, it should be noted that for simplicity and conciseness this has not been used throughout. For completeness, all similar features from all embodiments are interchangeable unless it is specified to the contrary herein.

An advantage of this arrangement, namely of the biological tissue of the limb abutting the inner surface of the cap portion, is that it minimizes the space between the prosthetic interface device 400 and the tissue. Without wishing to be bound by theory, it is believed such minimization reduces the risk of infection, edema or internal tissue necrosis.

Figure 5A:
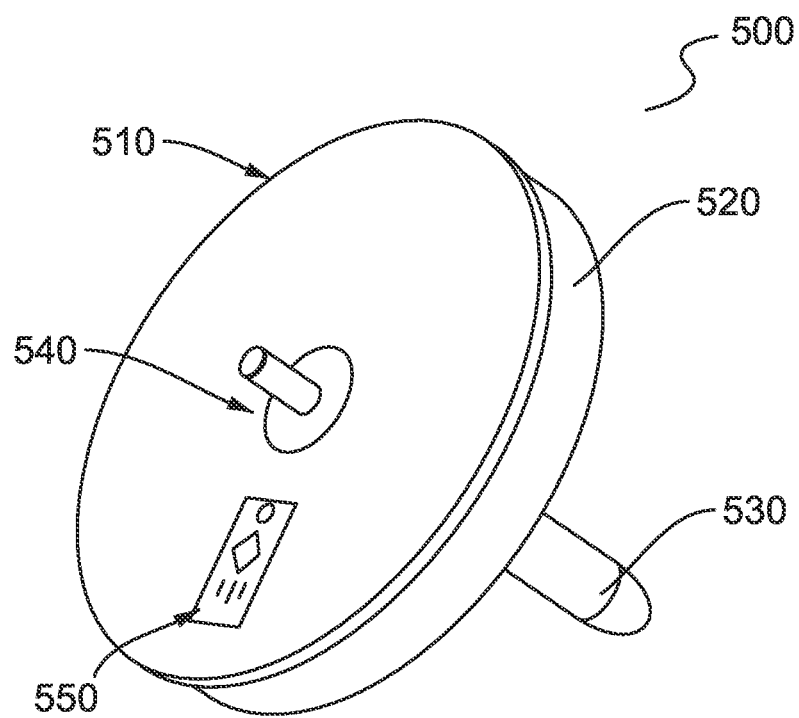
FIG. 5A illustrates a top view of the prosthetic interface device according to one embodiment.
Figure 5B:
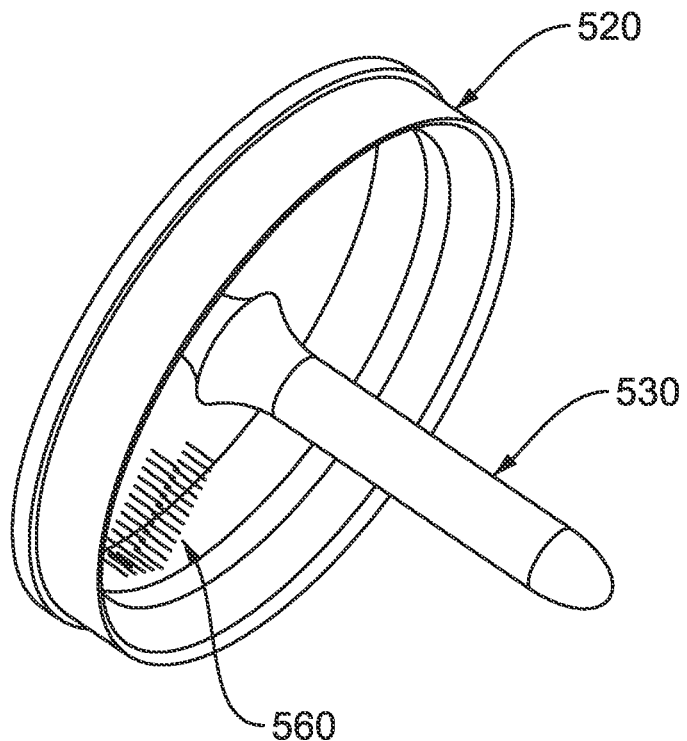
FIG. 5B illustrates a bottom view of the prosthetic interface device of FIG. 4A.

FIG. 5A illustrates a top view of the prosthetic interface device according to one embodiment. The prosthetic interface device 500 is comparable to prosthetic interface device 400 and prosthetic interface device 100 and therefore features of these embodiments (and further embodiments described below) should be considered to be additional and/or interchangeable. The prosthetic interface device 500 comprises a surface 510 with a surrounding flange 520. The surrounding flange may comprise a biocompatible material similar to that described earlier that allows the skin to interface with the prosthetic interface device 400.

The prosthetic interface device 500 in this embodiment further comprises a stem portion 530 that in use is inserted into the bone to transmit biomechanical loads. It will be appreciated that the stem portion 530 may be integral with or simply connectable to surface portion 510. In this example, the stem portion 530 comprises a metal bar 540 for engagement with a prosthetic connector, similar to embodiments described previously. The bar 540 need not comprise metal nor need it be a bar. Indeed, this component may comprise any shape or arrangement suitable for engagement with a prosthesis or prosthetic connector.

The prosthetic interface device 500 in this embodiment further comprises an electronics unit 550. This electronics unit 550 may detect and process nerve signals (e.g. neural processing for neural control and/or communication and/or patient health monitoring). It will be appreciated that one or more electronics units may be provided and that the electronics unit 550 may not be required to be flush on the surface 510 of the prosthetic interface device 500 or even be integral with the prosthetic interface device 500.

The electronics unit 550 may detect and process nerve signals and/or may be configured to simply transmit these signals to a remote processor by means of a transmitter/transceiver. The electronics unit 550 may comprise internal electrical connectors for one or two way connection to the central nervous system (via for example, additional internal electrodes 560 as detailed in FIG. 56).

Figure 6:
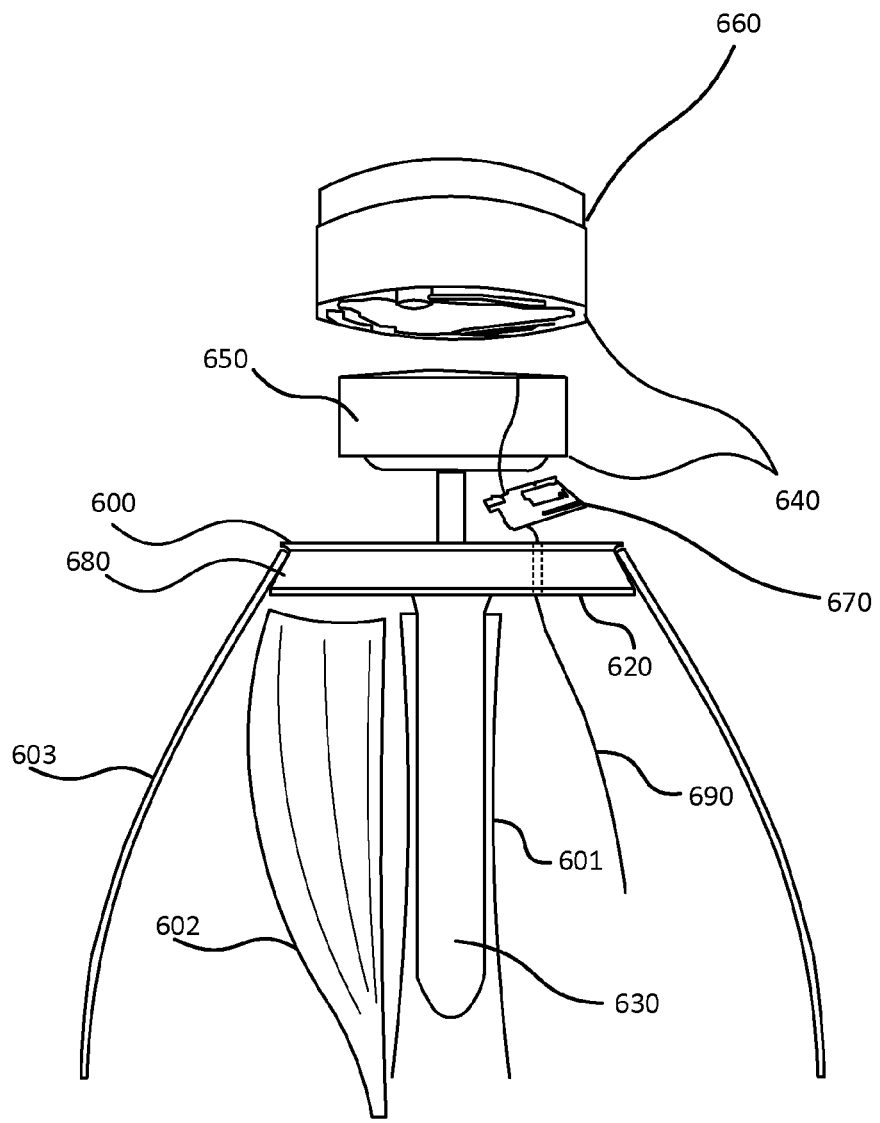
FIG. 6 depicts a side view of the prosthetic interface device according to one embodiment when in use and particularly when configured for connection with a prosthesis.

In this embodiment, the electronics unit 550 comprises a small microprocessor board embedded to process neural signals, internally this will be connected via wires crossing through the cap portion at ports as demonstrated in FIG. 6 to a nerve cuff or subcutaneous electrode pads (not shown).

FIG. 56 illustrates a bottom view of the prosthetic interface device of FIG. 5A. As described above, the prosthetic interface device 500 comprises a surface 510 with a surrounding flange 520 and stem portion 530.

The surrounding flange 520 allows the skin to interface with the prosthetic interface device 500 and may comprise the materials and have the configuration described in respect of surrounding flange/edge 210 or otherwise described herein.

The prosthetic interface device 500 aims to utilise an osseointegrated connector or stem portion 530 and a skin-integrated cap portion 200 or 510 and 520 to attach to an amputated limb. An advantage is that the prosthetic interface device 500 provides a strong mechanical attachment between the skin and the prosthetic interface device 500 which in turn provides a number of other distinct advantages.

Further advantages include that the improved mechanical connection reduces the risk of skin-implant separation and hence lowers the chance of infection occurring; having a cap portion that is substantially larger than the stem, possibly up to the full width of the limb, reduces the need for a stump to be formed prior to fitting the device, opening up the possibility for the device to be implanted in the same surgery as the amputation (current devices require one or two follow on surgeries after the initial amputation surgery); and having a cap portion that spaces the skin interface from the stem provides space to modularise the connection by providing a surface for ports across the cutaneous barrier (described in more detail below) and allows space for neural processing on board the limb rather than on board the prosthetic as in current devices. The modularity of the cap from the stem allows a customizable geometry of the prosthetic interface device cap 500 and the microstructure present at the prosthetic interface device skin integration site 520 minimize stress concentrations at the skin-cap junction and hence instances of failure which translates to the prosthetic interface device 500 having improved mechanical performance with the soft tissue.

FIG. 6 depicts a side view of the prosthetic interface device according to one embodiment when in use and in particular when configured with a prosthetic connector for connection with a prosthesis. The prosthetic interface device 600 is comparable to prosthetic interface device 100, prosthetic interface device 400 and prosthetic interface device 500 and therefore features of these embodiments (and further embodiments to follow) should be considered to be additional and/or interchangeable.

The prosthetic interface device 600 in this embodiment further comprises a stem portion 630 that in use is inserted into the bone 601 to transmit biomechanical loads. It will be appreciated that the stem portion 630 may be integral with or simply connectable to the cap portion of the prosthetic interface device 600.

The stem portion 630 may be connectable to a prosthetic connector 640 which is configurable to receive a prosthesis. The prosthetic connector 640 may be integral with or connectable to the stem portion 630, and where it is connectable, may be connectable by any suitable means, e.g. threaded configuration, compression fitting, bayonet, etc. In some embodiments, the connector may comprise a safety mechanism, for example to protect the bone from extreme loads.

An advantageous feature of the prosthetic interface device 600 and prosthetic connector 640 is the interchangeability of components. Because both the cap portion of the prosthetic interface device 600 and the prosthetic connector 640 are attached to the stem portion via a simple threaded connection or otherwise, a future design revision of any part will not invalidate any other and/or will not require further major surgery.

In this embodiment of the invention, the prosthetic connector 640 may comprise female and male connector portions. In this exemplary embodiment, the male portion 650, which may comprise an electrical connection, may be affixed to the stem portion 630 whereas the corresponding female portion 660 may affix to or be connectable with the prosthesis.

It will be appreciated that the prosthetic connector 640 may comprise at least 2 or more parts and may have any arrangement suitable for allowing connection between the stem portion and the prosthesis.

In an alternative embodiment, the prosthetic connector may be a male connector. It will be appreciated that the prosthetic connector need not be a male connector but simply needs to provide means for facilitating connection between the prosthetic interface device 600. The prosthetic connector in this embodiment is adapted to connect to a prosthesis having a female connector; although it will be appreciated that the prosthesis also need not have a female connector, but simply needs to be configurable to attach to the connector provided on the stem portion.

In embodiments where an electrical connection is provided between the amputated limb and the prosthesis, the connection allows for transference of information, for example output neural data from nerve signals or otherwise gathered from the limb via a nerve cuff, through an on board microprocessor 670 (optional) to the prosthesis (also optional) via the connector 640 and preferably in some embodiments provide sensory neural feedback from the prosthesis to the limb.

It should be noted that in although in one exemplary embodiment data is only flowing out from the neurons via the electrical connection to the prosthesis for the purpose of motor control of the prosthesis, there are many feasible additional or alternative embodiments in which this same subsystem may handle sensory data captured by the prosthesis and feeds it back into the neural system of the limb. Where there is feedback, it will be appreciated that similar hardware may additionally be used as that for known systems of neural detection.

The prosthetic interface device 600 in this embodiment further comprises an access port 620. The access port 620 may comprise any dimension and more than one access port 620 may be provided in respect of the prosthetic interface device 600.

The access port 620 may provide access for drainage and/or other biosensing or functionalised materials. The one or more access ports 620 may comprise on or more of the following functions:

Passage of biosensors for detecting biofilm formation, edema or other conditions;

Passage of cables carrying electrical data for control of any device connected to the prosthetic connector, these cables may be internally connected to nerve cuffs or muscle activation sensing electrodes or other electrical connections to or from the nervous system or other internal tissues;

An aperture through which fluids or gasses can be passed either continuously, periodically or in a single instance either through the port directly or through a conduit that passes through the port for purposes including the promotion and maintenance of tissue health by mechanical stimulation, nutrient flow or other means;

Access for surgical procedures including keyhole surgery, this may include for care of the inside of the stump and/or to remove, update, replace and/or reposition internal components of the prosthetic interface device, specifically the nerve cuff; and Access for other medical procedures including but not limited to administering of medicines, draining of edema fluid in the stump or care of internal tissues.

In an embodiment, the wires or cables 690 carrying electrical data for control of any device connected to the prosthetic connector 640, optionally via the processor 670, may be internally connected to nerve cuffs or muscle activation sensing electrodes or other electrical connections to or from the nervous system or other internal tissues. It will be appreciated that these wires or cables 690 can connect directly to the biological tissue, for example muscle 602, without going through any bone (e.g. without needing to go through the stem portion when osseointegrated).

These electrodes may comprise a shape, material and/or particular properties, mechanical or otherwise, which are biocompatible and minimize tissue reaction. Additionally, these electrodes may be selected to minimize tissue damage caused from chemical reactions, toxicity or otherwise. Examples of suitable muscle and/or nerve based electrodes include cuff, needle, sieve or micro array electrodes and/or implantable myoelectric sensors or similar.

The types of analysis that can be conducted on neural and/or muscular data can include any one or more of: individual nerve and muscle activations; analysis of groups of muscles and nerves; dynamics of firing patterns of nerves or muscles including the timing of firing such as frequency, rate, interval, shape of firing signal and the distribution pattern across the population of neurons; and the overall changes in electrical potential of the tissue at one or more sites anywhere within the limb. It should be noted that combinations of any or all of the above may be used simultaneously to improve data quality and that which types of analysis are under use may change dynamically.

In this embodiment, cap edges 680 are concave and comprise further angled flanges for skin 603 integration. It will be appreciated that the side flanges 680 need not be angled, straight nor stiff and/or need not comprise flanges. However, in this preferable arrangement the skin engages with the substantially the entire side flange 680 of prosthetic interface device 600. This arrangement addresses the need to ensure maintenance of homeostatic barrier which avoids/prevents infection of bone implant. In a preferred embodiment, as mentioned above, the inner surface of cap portion 605 of prosthetic interface device 600 abuts the biological tissue of the amputated limb.

The parameters of the flange 680 which may be customizable including the following: the angle ($\theta$), length ($l$), flange thickness, geometry of the interface surface, number size and location of cross flange holes, pore structure (size and density), curvature radii and/or relative sizing of sections of the overall profile of the flange cross-section which will be described in further detail in respect of FIGS. 8A to 8E.

In some embodiments, the flange 680 may comprise hydroxyapatite and/or any other material which promotes growth and/or integration of tissue groups.

Figure 7:
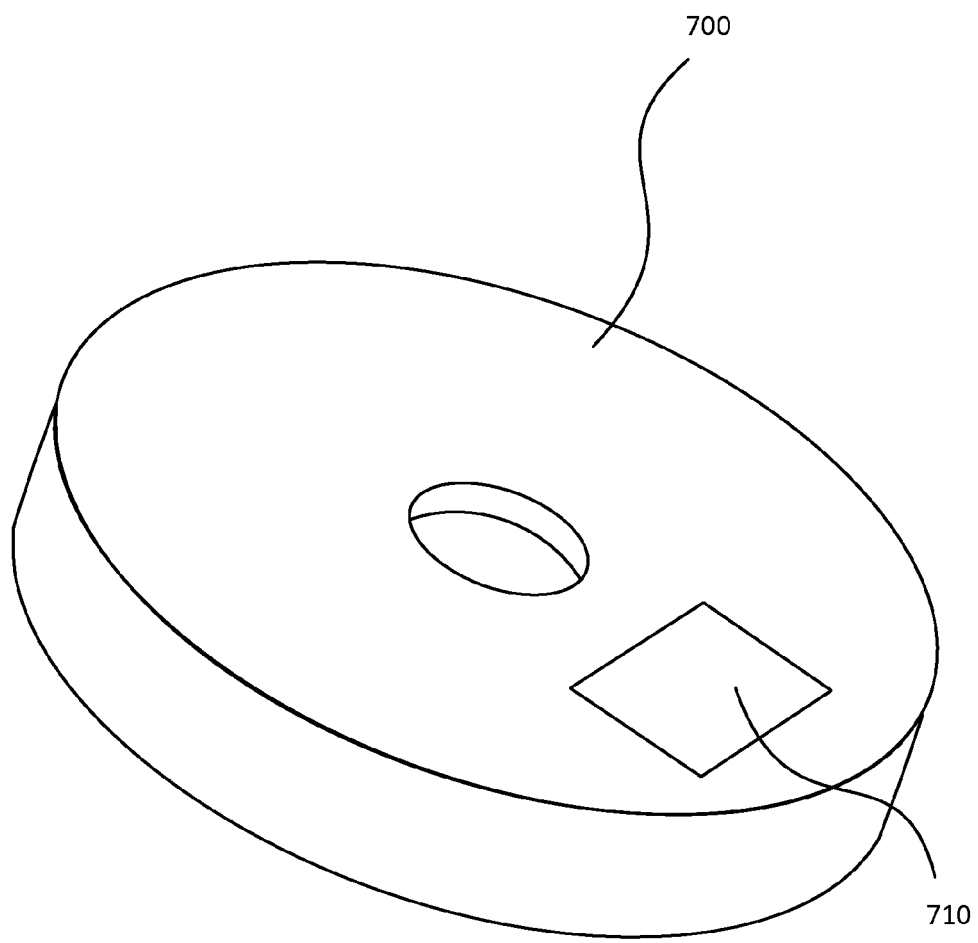
FIG. 7 depicts a top view of the cap portion of the prosthetic interface device comprising on board electronics suitable for neural processing and/or monitoring according to one embodiment.

FIG. 7 depicts a top view of the cap portion of the prosthetic interface device according to one embodiment. The prosthetic interface device 700 is comparable to prosthetic interface device 100, prosthetic interface device 400, prosthetic interface device 500 and prosthetic interface device 600 and therefore features described in respect of these embodiments (and all further embodiments) should be considered to be additional and/or interchangeable.

The prosthetic interface device 700 comprises an electronics unit or processor 710. The electronics unit 710 may be described as the brain machine interface in that it provides the connection between the prosthetic interface device 700 and the nervous system. Although in this embodiment the electronics unit 710 is fitted flush on the prosthetic interface device, in additional or alternative embodiments, the electronics unit or processor 710 may be comprised elsewhere, for example in the prosthetic connector, the prosthetic itself, etc.

The electronics unit 710 may be used to deliver sensing and control signals. Processing may therefore be integrated in the prosthetic interface device 700 itself. However, it will be appreciated that processing may be assisted by a further off board processor, for example, through an additional module housed in the attached limb or in a remote or local distinct unit.

The electronics unit 710 may have two functionalities: (i) it may take signals from neural data coming through the ports (described above) and processes it to make it readable as a control signal by the prosthesis; and/or (ii) it may take data from: biosensors from the ports (described above), its own internal accelerometer and/or gyroscope, strain gauges within the cap portion and/or stem portion and/or prosthetic connector. In one embodiment, the electronic unit 710 logs or otherwise processes and stores key data from which can be made available to the healthcare provider as an on going service to monitor device health, stump health, possible instance of extreme load etc. This additional functionality may be provided wirelessly, through near field technologies or otherwise. It will be appreciated that it is not necessary that the electronics unit 710 perform every function of the processing.

For example, in an additional or alternative embodiment, the processing may be (additionally) conducted via a remote processor (in the prosthesis or otherwise), electronics unit 710 comprising a transmitter and/or transceiver to facilitate this arrangement.

The electronics unit 710 may optionally further comprise a battery. Preferably, this battery is a long-life battery. The battery may be rechargeable and/or may be interchangeable. In additional or alternative embodiments, power to the electronics unit may be provided from the prosthesis (for example via the electrical connection detailed in respect of FIG. 6 or similar).

It will be appreciated that the hardware and/or software of electronics unit 710 may be updated at any time. It is feasible that the hardware and/or software of the electronics unit 710 along with the prosthetic connector (as described above) may be updated or replaced at any time while the prosthetic interface device 700 remains implanted in the patient; this is facilitated as neither component interacts directly with any biological tissue. It will be appreciated with this arrangement, the hardware of the neural connector on the interior of the stump may be updated with a minimally invasive surgery through one of the ports of the cap (described above), as may any biosensors which sit either occupying a port or possibly on the internal surface.

FIGS. 8A to 8E depicts a cross-sectional side view of the prosthetic interface device and specifically the skin integration portion of the device according to various embodiments when in use. The prosthetic interface device 800 depicted in these figures are comparable to prosthetic interface device 100, prosthetic interface device 200, prosthetic interface device 400, prosthetic interface device 500, prosthetic interface device 600 and prosthetic interface device 700 and therefore features described in respect of these embodiments should be considered to be additional and/or interchangeable.

In these embodiments, the cap portion 820, comparable to the aforementioned cap portions, comprises an angled flange of skin integration. Revolved around the centre line on the right hand side, the diameter of revolution may vary around the prosthetic interface device 800 to allow matching to limb cross-section. Indeed, cap portion 820 need not be circular or even substantially circular. Further, the cap portion 820 may comprise an open cell porous structure for skin integration as described above.

Figure 8A:
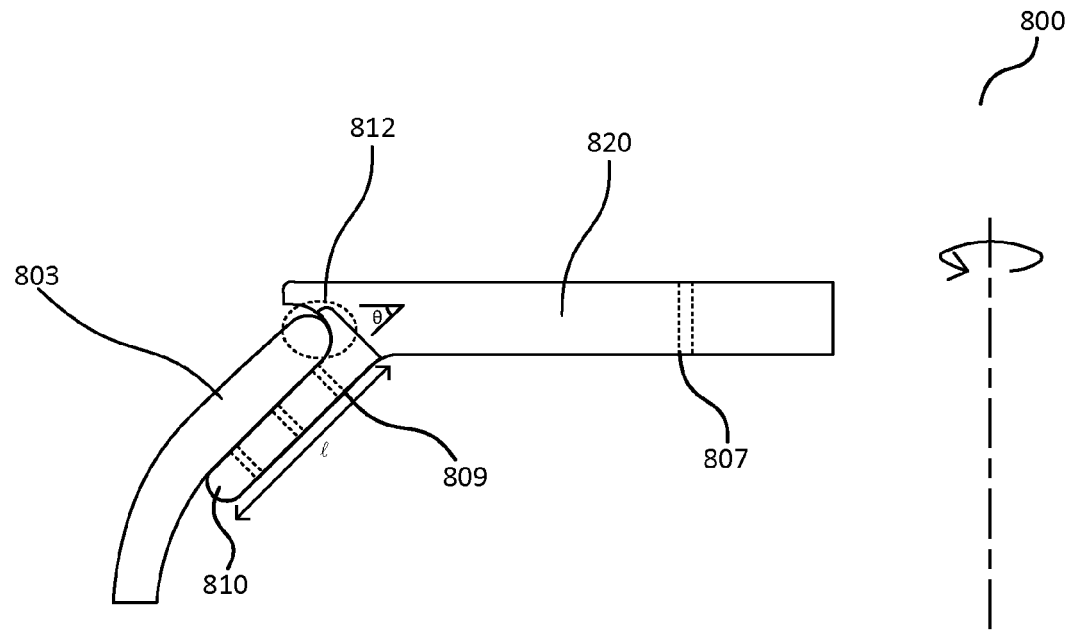
FIGS. 8A to 8E depict cross-sectional side views of the prosthetic interface device and specifically the skin integration portion of the device according to various embodiments when in use.

FIG. 8A depicts a cross-sectional side view of the prosthetic interface device 800 and specifically the skin integration portion of the device 800 when in use according to one embodiment.

In this embodiment, side flange 810 is angled to enhance skin 805 integration. It will be appreciated that the side flange 810 need not be angled. However, in this preferable arrangement the skin 803 engages with the substantially the entire length of side flange 810 of prosthetic interface device 800.

This arrangement ensures maintenance of homeostatic barrier which avoids/prevents infection of bone implant when prosthetic interface device 800 is in use.

The parameters of the flange 810 which may be customizable including the following: the angle (0), length (I), flange thickness, geometry of the interface surface (region A), number size and location of cross flange holes, pore structure (size and density), curvature radii and/or relative sizing of sections of the overall profile of the flange cross-section.

In this embodiment, the geometry of skin interface surface 812 is concave and rounded. Indeed, the interface surface in this embodiment is formed from a carve out of the lower surface of the cap portion 820 and the flange 810 extending therefore such that the upper surface of the cap portion 820 so as to encase or shield the skin of the limb when in use. It will be appreciated that this upper extension of the cap portion need not be provided or can be modified, for example to include an additional flange protruding therefrom which may be provided protruded in a substantially parallel manner to flange 810 with similar, smaller or larger dimensions thereto or with any other dimensions or orientation.

The flange 810 in this embodiment protrudes beyond the radius of the cap portion 820, but it will be appreciated that in use, this protrusion will be provided substantially underneath the skin/within the limb and therefore will not be visible. It will also be appreciated that although the flange 810 may be integral with the cap portion 820, it need not be and in fact can be distinct therefrom but fixable or attachable thereto.

In each of FIG. 8A to 8E, dotted lines 809 crossing the flange 810 are provided. It is the intention that in addition to the flange 810 being constructed of an open cell porous material where preferably the skin tissue can grow into from the above and muscle tissue can grow into from the interior surface, a number of holes or conduits 830 may be provided, at for example regular positions on the flange 810, that pass all the way through the porous flange 810. These holes or conduits 830 are designed to provide a channel for nutrient flow between the skin tissues on the outer surface of the flange 810 and the muscle on the inner surface. Although three holes or conduits 830 are depicted, it will be appreciated that any number, spacing and size may be provided.

It will also be appreciated that such holes or conduits 830 are not required. Indeed, because flange 810 comprises a porous structure there is the ability for nutrients in fluid to transfer across the flange 810 such that the skin tissue on the outer surface which in this configuration would ordinarily be isolated from the other tissues can receive nutrients from the bulk muscle tissues on the inside of the limb. However, to further aide in nutrient transfer, it is the intention that in addition to the flange 810 being bulk porous that there are specific holes or conduits 830 that individually cross the full thickness of the flange 810 so as to allow a freer flow of fluid and nutrients across the flange 810.

In one example, the size of the conduits or holes can range from 800 um to 1 mm. However, it will be appreciated that the conduits can be 850 um, 900 um, 950 um, 1.05 mm, 1.1 mm, 1.15 mm, 1.2 mm, 1.25 mm or any dimension in between.

It will be appreciated that flange 810 constructed by a number of methods including, but not limited to wire sintering, bead sintering, 3D printing, chemical etching or otherwise or metal casting with void creating materials. Selection of the design of the flange 810 can be made considering one or more of the following parameters: surface properties of the flange 810 including stiffness and surface tension, the mean asperity sizes, overall density and solid and/or fluid permeabilities.

Figure 8B:
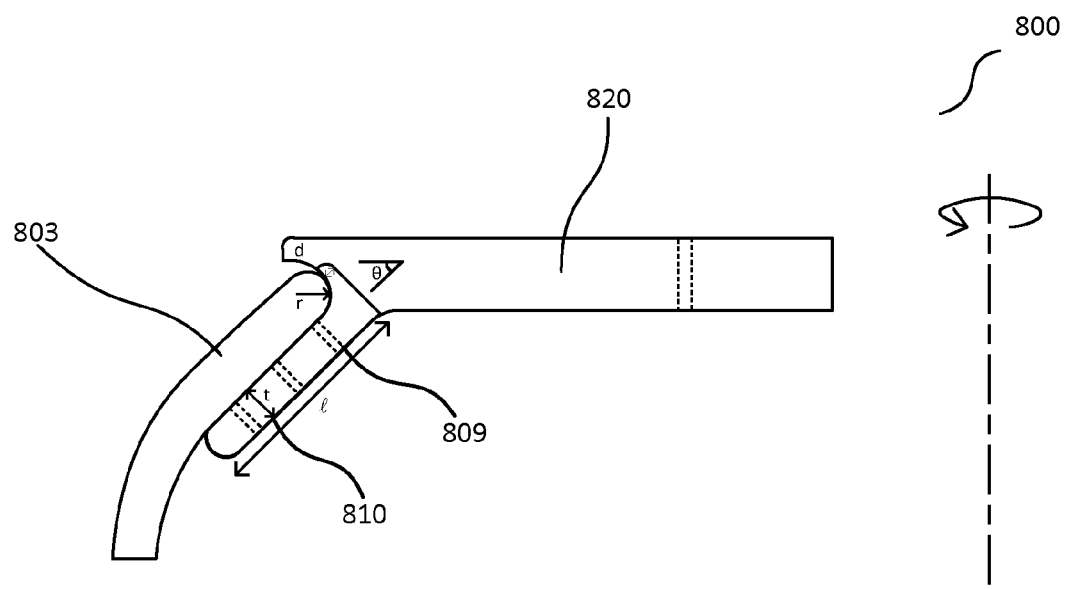

FIG. 8B depicts a cross-sectional side view of the prosthetic interface device 800 and specifically the skin integration portion of the device 800 illustrated in FIG. 8A.

The parameters shown in FIG. 8B are not exhaustive but comprise some parameters to defining the shape of the skin interface portion of the cap 820. In the initial embodiment the flange 810 is at a 45 degree angle to the cap 820, is 15 mm long and 3 mm thick being constructed of pores that will be in the 200 um to 300 um range. The radius of curvature where the flange 810 meets the surface of the cap portion 820 (also where the free edge of skin is likely to be positioned), known as the skin interface portion indicated by reference 812 of FIG. 8A) is 5 mm and the pores penetrate 2 mm into the surface of the skin interface portion.

Although in this example, the flange 810 is at a 45 deg angle to the cap 820, the flange 810 may be angled at any degree, for example at or less than 90 deg, at or less than 80 deg, at or less than 70 deg, at or less than 60 deg, at or less than 50 deg, at or less than 40 deg, at or less than 30 deg, at or less than 20 deg, at or less than 10 deg or any intermediate thereof see FIGS. 9A to 9D for some exemplary embodiments.

Although the flange 810 in this embodiment is exemplified as being 15 mm long and 3 mm thick, the flange may be any length including 5 mm, 10 mm, 20 mm, 25 mm, 30 mm to 35 mm or any intermediate thereof and may be any thickness ranging from less than 1 mm, less than 2 mm, less than 3 mm, less than 4 mm to less than 5 mm.

Although in this embodiment, it is described that the flange 810 is constructed of pores, it will be appreciate that the flange 810 is constructed of pores, the flange need not to be entirely constructed of pores but rather may be substantially constructed or may comprise areas or portions thereof having pores.

Although it exemplified that the pores that will be in the 200 pm to 300 p.m range, the pores may be of any size ranging from 30 p.m to 800 p.m. It will appreciated that the pore size may or may not be uniform and/or the porosity may extend any part or substantially all of the flange 810 and/or skin engagement interface portion. In some embodiments, the pore sizes range from 100 pm to 750 pm, 150 pm to 700 pm, 200 pm to 650 pm, 250 um to 600 um, 300 pm to 550 pm, 350 pm to 500 pm, 400 pm to 450 pm or any combined or intermediate range thereof.

It is exemplified in this embodiment that the pores penetrate 2 mm into the surface of the skin interface portion. However, it will be appreciated that the pores may penetrate (i.e. the depth of porosity may be) less than 1 mm into the surface, less than 2 mm into the surface, less than 3 mm into the surface, less than 4 mm into the surface, less than 5 mm into the surface or any intermediate thereof.

The radius of curvature of the skin interface portion is exemplified in this embodiment as 5 mm. It will be appreciated that this radius can have any shape or dimension, but is preferably concave. The radius may be 1 mm, 2 mm, 3 mm, 4 mm, 6 mm, 7 mm, 8 mm, 9 mm, 10 mm or any intermediate thereof and may account for the thickness of the cap 820.

Figure 8C:
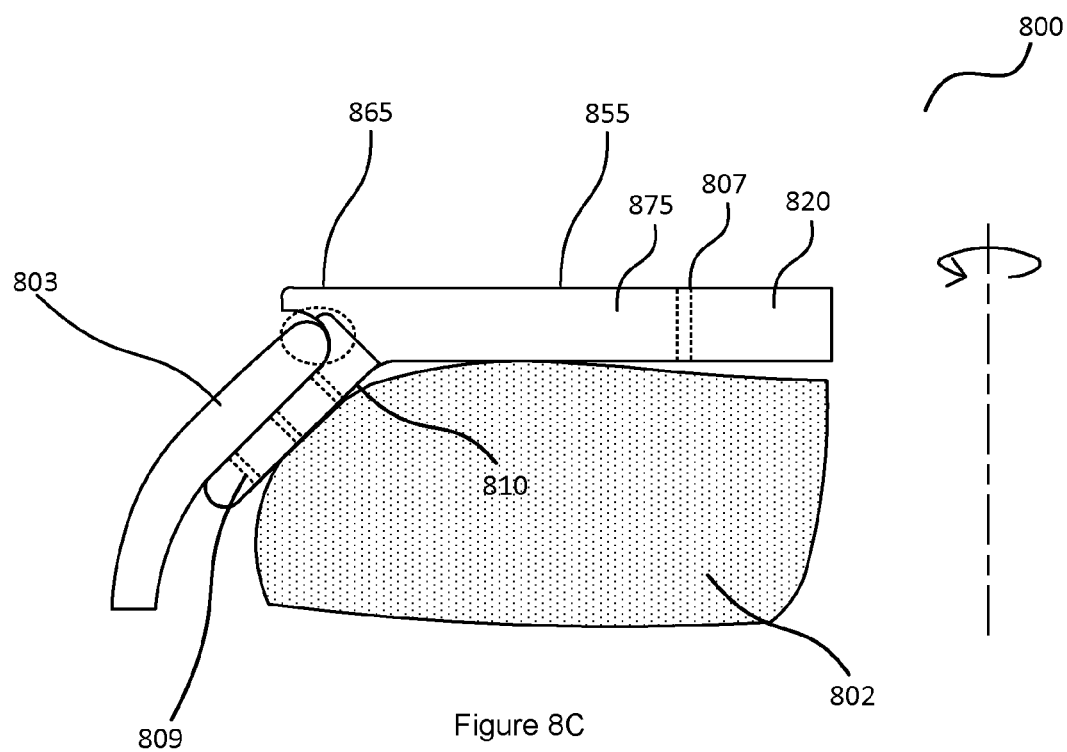

FIG. 8C depicts a cross-sectional side view of the prosthetic interface device 800 and specifically the skin integration portion of the device 800 illustrated in FIGS. 8A and 8B.

In this embodiment, three surfaces of cap 820 are further defined, outer surface 855, skin interface surface 865 and inside surface 875.

The outer surface 855 of cap 820 is the top or outer surface that is not in contact with any tissue and is also not taking the load of a prosthesis. It will be appreciated that when in use, the cap 820 does not bear any load, but instead, the load bearing of any prosthesis is taken by the osseointegrated device (e.g. the stem portion).

The skin interface surface 865 of cap 820 is the curved section at the flange/cap junction that is where the leading edge of the skin tissue integrates.

The inside surface 875 of cap 820 is the inside surface of the cap which will be contacted by muscle tissue within the residual stump. It is expected that the muscle tissue will grow into the inner surface of the flange where it is porous and will meet the skin tissue in the middle of the porous flange. Where inside surface 875 is smooth the muscle will rest adjacent to the surface.

Figure 8D:
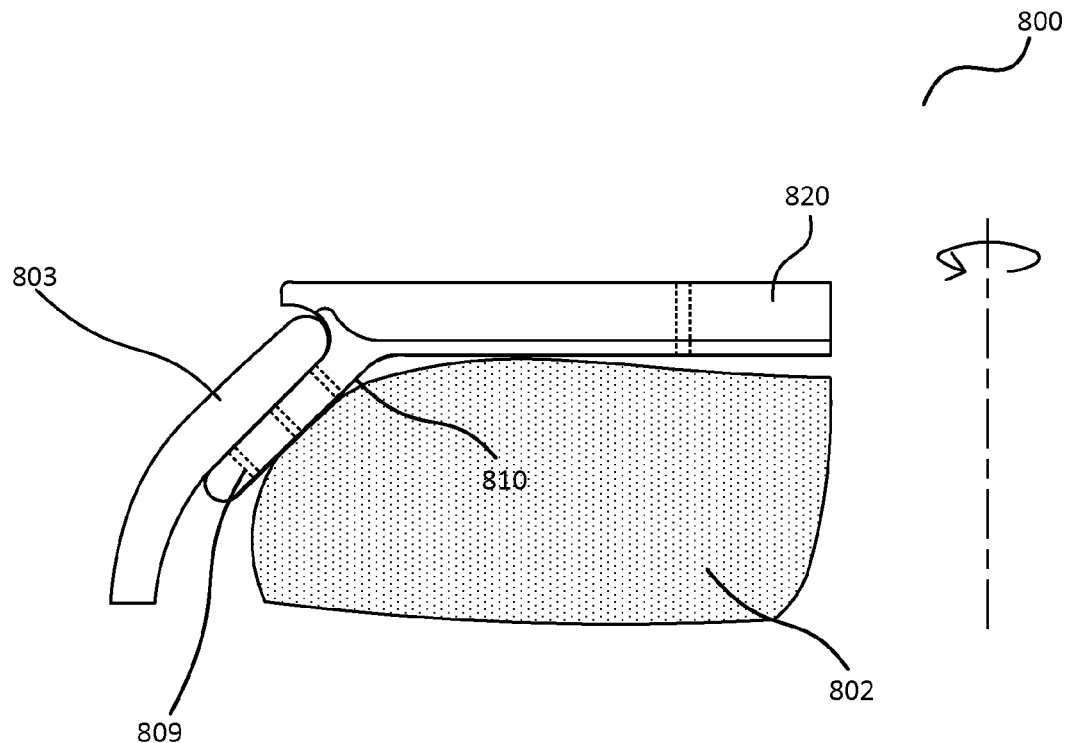

FIG. 8D depicts a cross-sectional side view of the prosthetic interface device 800 and specifically the skin integration portion of the device 800 of a further embodiment.

In this embodiment, the porous material comprising the flange extends along inside surface 885 of cap 820. This embodiment may be desirable in order to promote muscle integration into the whole inner surface of the cap 820 so as to reduce the possibility of tissue shrinkage away from the cap and formation of a void where edema can occur.

It will be appreciated that the porosity along the inside surface 885 of the cap 820 may be the same or different from the porosity of the flange. The same dimensions and geometry described above as being adaptable dimensions in respect of the flange to promote skin integration, may be equally applicable in respect of the inside surface 885 of the cap 820 to promote muscular integration and/or other biological tissues in the amputated limb.

Figure 8E:
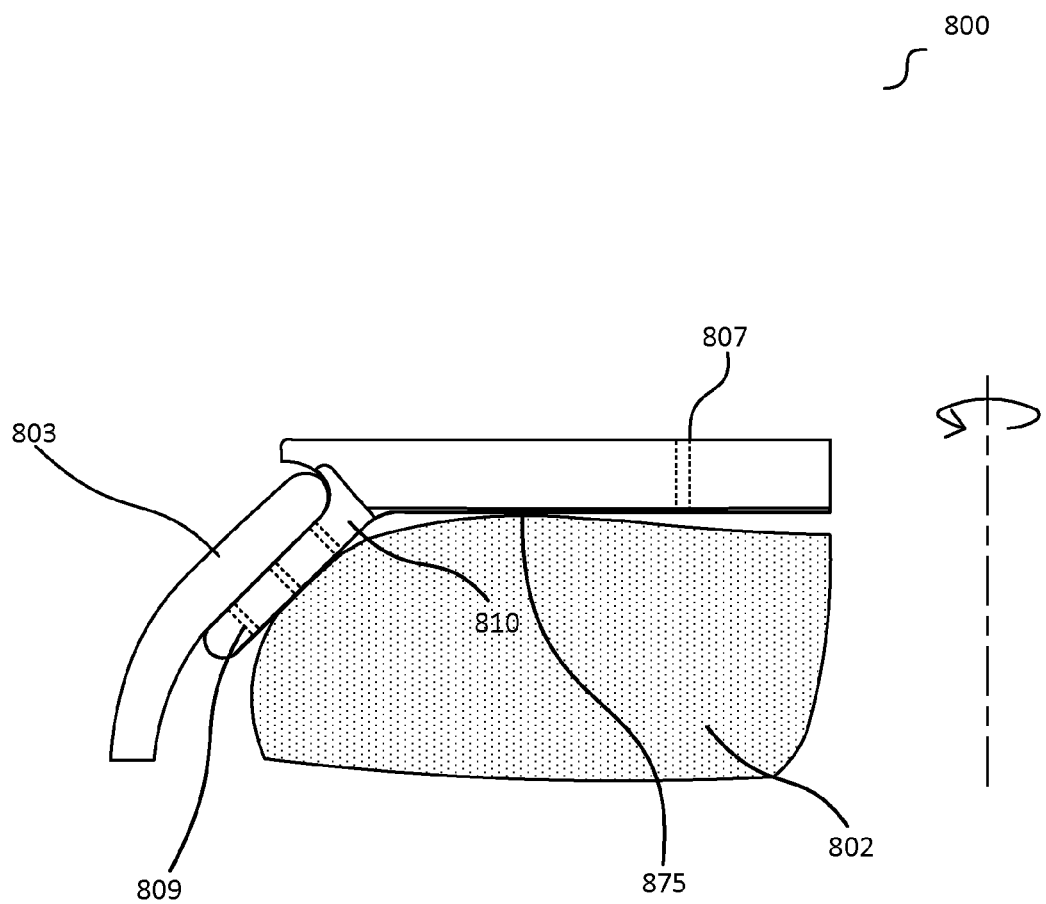

FIG. 8E depicts a cross-sectional side view of the prosthetic interface device 800 and specifically the skin integration portion of the device 800 in an additional or alternative embodiment to FIG. 8D.

In this embodiment, the inner surface 885 of cap 820 is either functionalized with a drug eluting surface or other surface coating to promote a favourable response of the contacting muscle tissue. For example, the inner surface 885 can be texturized to comprise the same or a different porosity then the flange. Alternatively, the porosity of the inner surface 885 can be selected to facilitate integration with the vascular and/or muscular tissue etc. abutting thereto.

By functionalized, we include any surface that is chemically altered for example including specific material chemically altered to act as a drug binding site, to act in an anti-inflammatory capacity, and/or to act as an antibiotic. Additionally or alternatively, the inner surface 885 may be drug eluting. In one exemplary embodiment, the inner surface 885 may comprise one or more layers of coating which serves to hold and release a drug by contract transfer. For example, the inner surface 885 may be adapted to provide a slow release of one or more inflammatory drugs. These may be released in a long acting manner, and indeed in some embodiments the inner surface 885 may be biodegradable such that one all drug has been released, the surface degrades.

FIGS. 9A to 9D illustrate a cross-sectional side view of exemplary geometries of the prosthetic interface device, specifically the skin interfacing portion thereof according to various embodiments when in use.

Figure 9A:
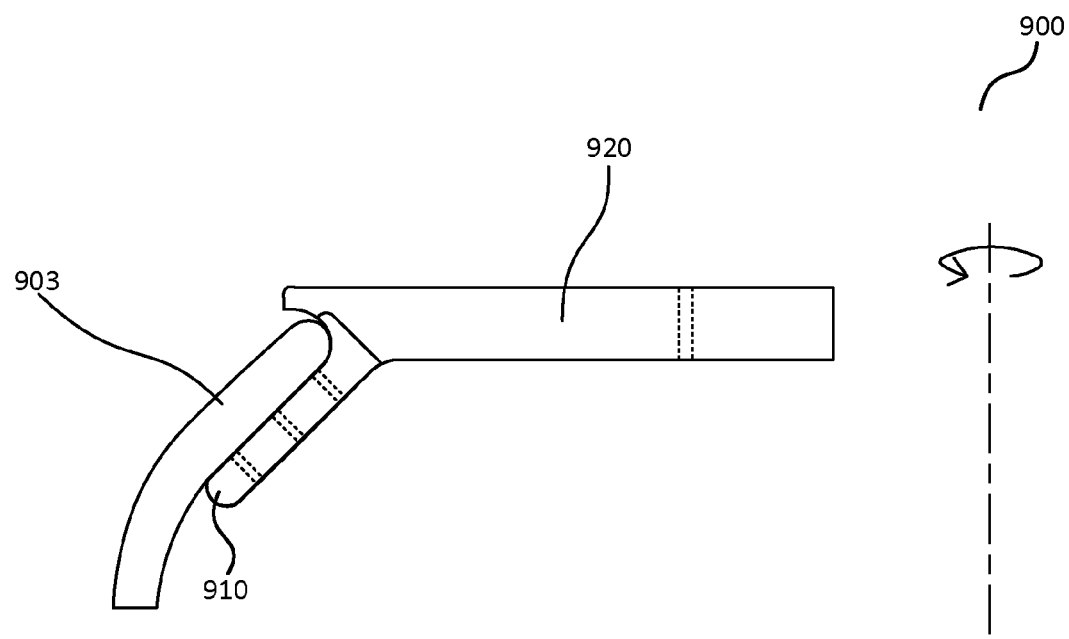
FIGS. 9A to 9D illustrate a cross-sectional side view of exemplary geometries of the prosthetic interface device according to various embodiments when in use.

FIG. 9A illustrated a cross-sectional side view of prosthetic interface device 900 when in use and attached to the skin 903 of a patient's limb, where flange 910 is angled at a 45 degree angle with respect to the surface of the cap portion 920.

Figure 9B:
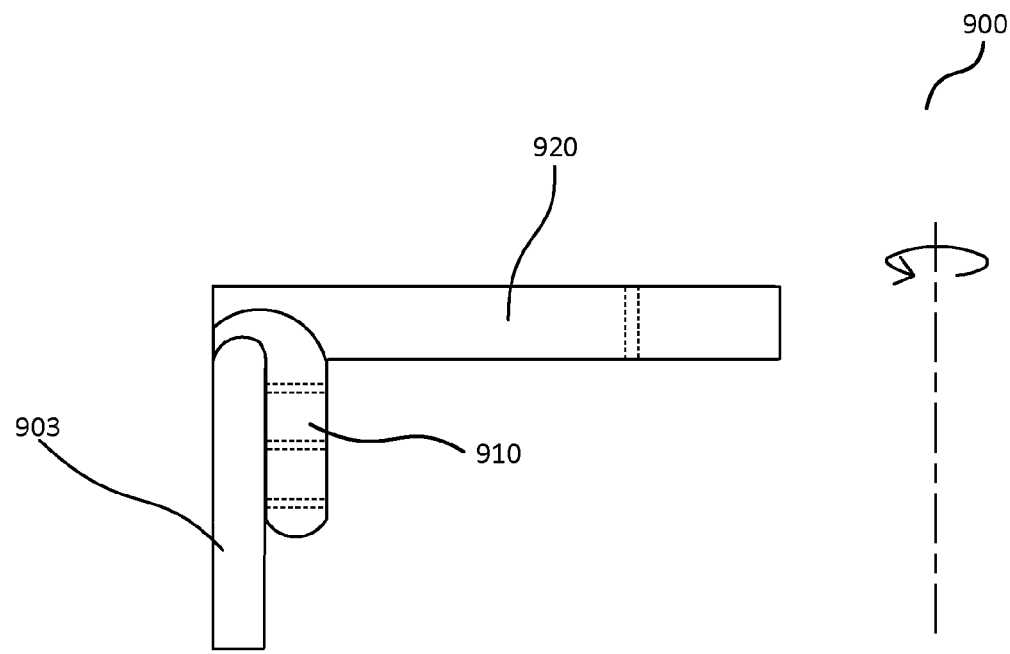

FIG. 9B illustrated a cross-sectional side view of prosthetic interface device 900 when in use where flange 910 is angled at a 90 degree angle with respect to the surface of the cap portion 920.

Figure 9C:
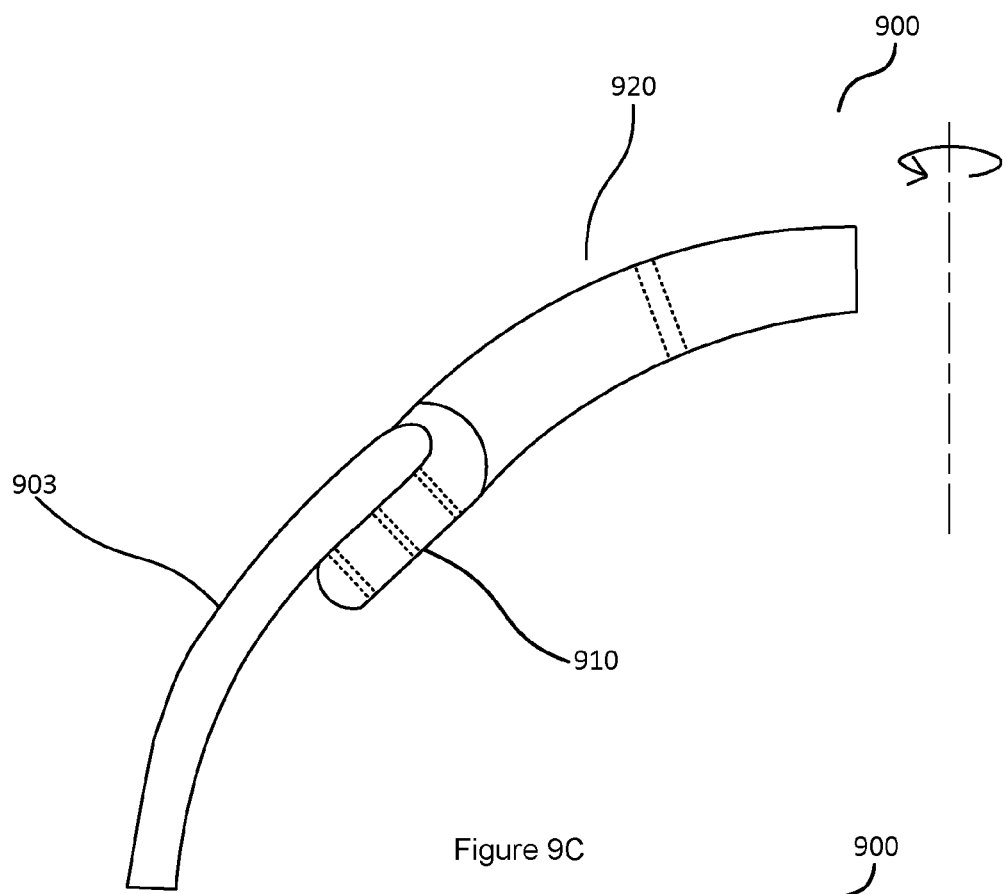

FIG. 9C illustrated a cross-sectional side view of prosthetic interface device 900 when in use where the surface of the cap portion 920 has a domed or rounded shape.

Figure 9D:
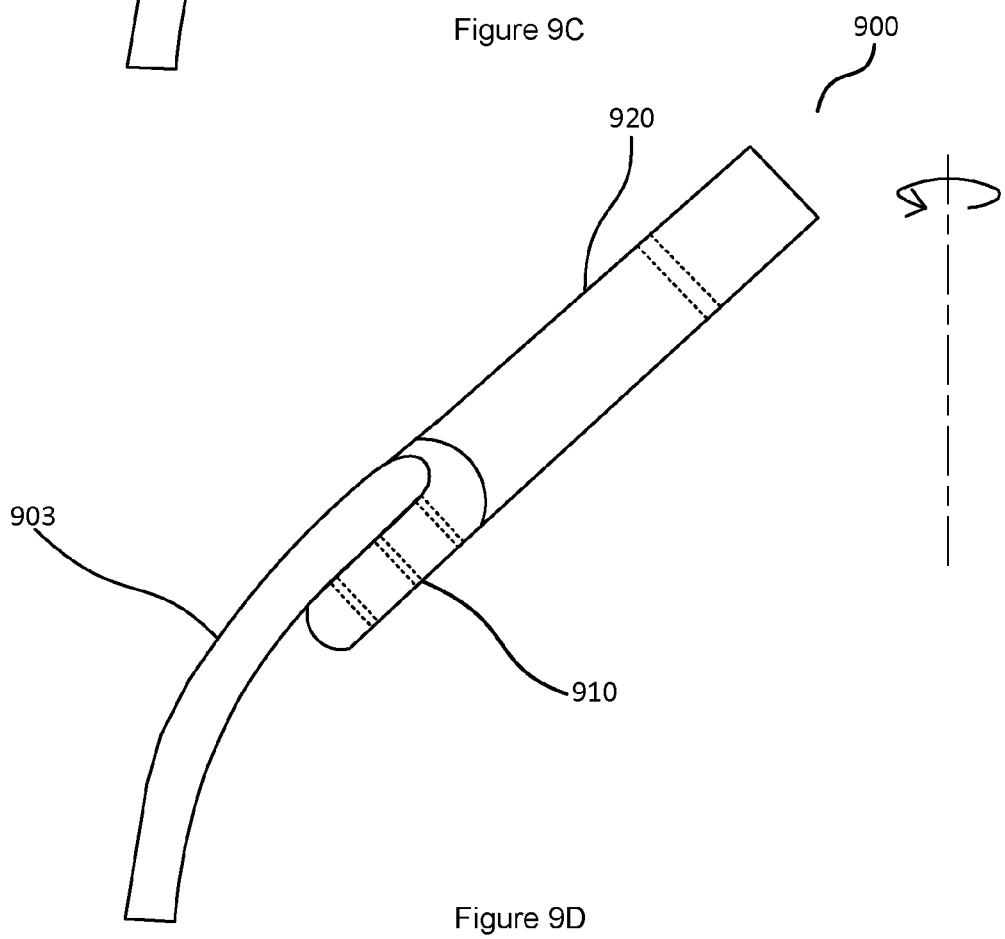

FIG. 9D illustrated a cross-sectional side view of prosthetic interface device 900 when in use where the surface of the cap portion 920 has a conical or pointed shape.

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

What is claimed is:

1. An osseointegrated interface device for engagement with an amputated limb and skin of the amputated limb comprising:
   a cap portion engageable with an osseointegrated device;
   wherein the cap portion comprises a surrounding flange;
   wherein the surrounding flange is configured to receive the skin of the amputated limb such that
   the received skin of the amputated limb by the surrounding flange is spaced from the osseointegrated device by a surface area of the cap portion; and
   wherein the surface area of the cap portion is configured to facilitate access to the interior of the amputated limb at a distance from the osseointegrated device.

2. The device of claim 1, with the osseointegrated device further comprising a stem portion engageable with the cap portion.

3. The device of claim 1, further comprising one or more ports.

4. The device of claim 1, further comprising one or more cables or wires carrying electrical data for control of a prosthesis.

5. The device of claim 1, further comprising an electronics unit to detect and/or process nerve signals.

6. The device of claim 1, wherein the distance between the surrounding flange and the osseointegrated device in is at least a portion of the radius of the amputated limb.

7. The device of claim 1, wherein the distance between the surrounding flange and the osseointegrated device is such that in use the skin received by the flange is not in contact with the osseointegrated device.

8. The device of claim 1, wherein the surrounding flange has dimensions which provide a homeostatic barrier about the amputated limb.

9. The device of claim 1, wherein at least one of the flange, the cap portion, and the device comprises a biocompatible material.

10. The device of claim 1, wherein the flange further comprises one or more conduits for providing nutrient flow between the skin and the tissue of the amputated limb, for example the muscle.

11. The device of claim 1, wherein the flange further comprises hydroxyapatite.

12. The device of claim 1, wherein the flange is constructed by wire sintering, bead sintering, 3D printing, chemical etching, or metal casting with void creating materials.

13. A device for engagement with an amputated limb and skin of the amputated limb comprising:
   a cap portion comprising a surrounding flange for engagement with the skin of the amputated limb;
   wherein the dimensions of the surrounding flange provide a homeostatic barrier about the amputated limb such that;
   the engaged skin of the amputated limb is spaced from an osseointegrated device by a surface area of the cap portion; and
   wherein the surface area of the cap portion is configured to facilitate access to the interior of the amputated limb at a distance from the osseointegrated device.

14. The device of claim 13, wherein the dimensions of the surrounding flange are adaptable.

15. The device of claim 13, wherein at least one of the flange, the cap portion, and the device comprises a biocompatible material.

16. The device of claim 13, wherein the flange further comprises hydroxyapatite.

17. The device of claim 13, wherein the flange is constructed by wire sintering, bead sintering, 3D printing, chemical etching, or metal casting with void creating metals.

18. The device of claim 13, wherein the device is engageable with the amputated limb via an osseointegrated device.

19. The device of claim 13, with the osseointegrated device further comprising a stem portion engageable with the cap portion.

20. The device of claim 13, further comprising one or more ports.

21. The device of claim 13, further comprising one or more cables or wires carrying electrical data for control of a prosthesis.

\* \* \* \* \*

UNITED STATES PATENT AND TRADEMARK OFFICE
CERTIFICATE OF CORRECTION

| | | |
|---|---|---|
| PATENT NO. | : 11,291,564 B2 | Page 1 of 1 |
| APPLICATION NO. | : 15/764307 | |
| DATED | : April 5, 2022 | |
| INVENTOR(S) | : Oliver Armitage | |

It is certified that error appears in the above-identified patent and that said Letters Patent is hereby corrected as shown below:

On the Title Page

Item (71) Applicant should read: -- BIOS Health Ltd. --.

Signed and Sealed this
Fourth Day of April, 2023

Katherine Kelly Vidal
*Director of the United States Patent and Trademark Office*